United States Patent
Jewett et al.

(10) Patent No.: US 9,951,392 B2
(45) Date of Patent: Apr. 24, 2018

(54) SUBSTRATE REPLENISHMENT AND BYPRODUCT REMOVAL IMPROVE YEAST CELL-FREE PROTEIN SYNTHESIS

(71) Applicant: Northwestern University, Evanston, IL (US)

(72) Inventors: Michael C. Jewett, Evanston, IL (US); Jennifer A. Schoborg, Evanston, IL (US); Charles Eric Hodgman, Evanston, IL (US); Mark J. Anderson, Wilmette, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/659,206

(22) Filed: Mar. 16, 2015

(65) Prior Publication Data

US 2015/0259757 A1     Sep. 17, 2015

Related U.S. Application Data

(60) Provisional application No. 61/953,275, filed on Mar. 14, 2014.

(51) Int. Cl.
*C12Q 3/00* (2006.01)
*C12P 21/00* (2006.01)
*C12P 21/02* (2006.01)

(52) U.S. Cl.
CPC ............. *C12Q 3/00* (2013.01); *C12P 21/00* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 5,494,810 A | 2/1996 | Barany et al. | |
| 6,337,191 B1 * | 1/2002 | Swartz | C07K 14/5255 435/6.15 |
| 7,338,789 B2 | 3/2008 | Swartz et al. | |
| 8,357,529 B2 | 1/2013 | Swartz et al. | |
| 2004/0209321 A1 | 10/2004 | Swartz et al. | |
| 2005/0054044 A1 | 3/2005 | Swartz et al. | |
| 2006/0211083 A1 * | 9/2006 | Katzen | C12P 19/34 435/68.1 |
| 2007/0154983 A1 | 7/2007 | Calhoun et al. | |
| 2008/0138857 A1 | 6/2008 | Swartz et al. | |
| 2008/0293150 A1 * | 11/2008 | Kohno | G01N 24/08 436/89 |
| 2011/0311679 A1 * | 12/2011 | Parenicova | A23C 19/0328 426/35 |
| 2012/0021950 A1 * | 1/2012 | Greiner-Stoeffele | C12N 15/1082 506/11 |
| 2012/0171720 A1 | 7/2012 | Church et al. | |
| 2014/0295492 A1 | 10/2014 | Jewett et al. | |
| 2015/0259757 A1 | 9/2015 | Jewett et al. | |
| 2016/0060301 A1 | 3/2016 | Jewett et al. | |
| 2016/0251336 A1 * | 9/2016 | Yang | A61K 47/48384 |
| 2016/0257946 A1 * | 9/2016 | Zimmerman | C07K 1/02 |

FOREIGN PATENT DOCUMENTS

WO     2014176469 A2     10/2014

OTHER PUBLICATIONS

Spirin, Trends in Biotechnol. 22, 10, 538-545, 2004.*
Tuite et al. Yeast 2:35-52, 1986 (Year: 1986).*
Hodgman et al., Biotechnol. Bioeng., 100(10):2643-2654, 2013 (Year: 2013).*
Wang et al., J. Biosci. Bioeng., 106(1):8015, 2008 (Year: 2008).*
Chapman, A. G., Fall, L, Atkinson, D. E., "Adenylate energy charge in *Escherichia coli* during growth and starvation." J. Bacteriol. 1971, 108:1072-1086.
Iizuka, N., Najita, L., Franzusoff, A, Sarnow, P., "Cap-dependent and cap-independent translation by internal initiation of mRNAs in cell extracts prepared from *Saccharomyces cerevisiae*." Mol. Cell. Biol. 1994, 14:7322-7330.
Ball, William J., et al., "Adenylate Energy Charge in *Saccharomyces cerevisiae* During Starvation", Journal of Bacteriology, vol. 121, No. 3, Mar. 1975, pp. 975-982.
Record, M. Thomas, et al., "Responses of *E. coli* to osmotic stress: Large Changes in Amounts of Cytoplasmic Solutes and Water", TIBS 23, Apr. 1998, pp. 143-148.
Record, M. Thomas, et al., "Biophysical Compensation Mechanisms buffering *E. coli* Protein-nucleic Acid Interactions against Changing Environments", TIBS 23, May 1998, pp. 190-194.
Underwood, Kelly A., et al., "Quantitative Polysome Analysis Identifies Limitations in Bacterial Cell-Free Protein Synthesis", Wiley Periodicals, 2005.

* cited by examiner

*Primary Examiner* — Nancy A Treptow
(74) *Attorney, Agent, or Firm* — Andrus Intellectual Property Law, LLP

(57) ABSTRACT

Methods and kits are provided for calibrating a cell-free protein synthesis reaction for optimal activity. The method includes the steps of providing an extract competent for cell-free protein synthesis (CFPS); performing cell-free protein synthesis with the extract; measuring a first reaction end-point where in vitro protein synthesis plateaus; measuring a second reaction end-point where Energy Charge of the extract declines to a level in a range from about 0.40 to about 0.80 of Energy Charge of a control extract; and adjusting Energy Charge of the extract to a level in a range from about 0.80 to about 1.0 of the control extract.

9 Claims, 17 Drawing Sheets

SEQUENCE LISTING

```
<160> NUMBER OF SEQ ID NOS: 6

<210> SEQ ID NO 1
<211> LENGTH: 2480
<212> TYPE: DNA
<213> ORGANISM: Artificial Sequence
<220> FEATURE:
<223> OTHER INFORMATION: SYNTHETIC PLASMID DNA (pY71sfGFP)

<400> SEQUENCE: 1
ggatcctgca gttgagatcc tttttttctg cgcgtaatct gctgcttgca aacaaaaaaa      60
```

```
ccaccgctac cagcggtggt tgtttgccg gatcaagagc taccaactct ttttccgaag    120
gtaactggct tcagcagagc gcagatacca aatactgtcc ttctagtgta gccgtagtta    180
ggccaccact tcaagaactc tgtagcaccg cctacatacc tcgctctgct aatcctgtta    240
ccagtggctg ctgccagtgg cgataagtcg tgtcttaccg ggttggactc aagacgatag    300
ttaccggata aggcgcagcg gtcgggctga acggggggtt cgtgcacaca gcccagcttg    360
gagcgaacga cctacaccga actgagatac ctacagcgtg agcattgaga aagcgccacg    420
cttcccgaag ggagaaaggc ggacaggtat ccggtaagcg gcagggtcgg aacaggagag    480
cgcacgaggg agcttccagg gggaaacgcc tggtatcttt atagtcctgt cgggtttcgc    540
cacctctgac ttgagcgtcg atttttgtga tgctcgtcag gggggcggag cctatggaaa    600
cgaattcaga tctcgatccc gcgaaattaa tacgactcac tatagggaga ccacaacggt    660
ttccctctag aaataatttt gtttaacttt aagaaggaga tatacatatg agcaaaggtg    720
aagaactgtt taccggcgtt gtgccgattc tggtggaact ggatggcgat gtgaacggtc    780
acaaattcag cgtgcgtggt gaaggtgaag gcgatgccac gattggcaaa ctgacgctga    840
aatttatctg caccaccggc aaactgccgg tgccgtggcc gacgctggtg accacccctga    900
```

```
ccaccgctac cagcggtggt tgtttgccg gatcaagagc taccaactct ttttccgaag    120
gtaactggct tcagcagagc gcagatacca aatactgtcc ttctagtgta gccgtagtta    180
ggccaccact tcaagaactc tgtagcaccg cctacatacc tcgctctgct aatcctgtta    240
ccagtggctg ctgccagtgg cgataagtcg tgtcttaccg ggttggactc aagacgatag    300
ttaccggata aggcgcagcg gtcgggctga acggggggtt cgtgcacaca gcccagcttg    360
gagcgaacga cctacaccga actgagatac ctacagcgtg agcattgaga aagcgccacg    420
cttcccgaag ggagaaaggc ggacaggtat ccggtaagcg gcagggtcgg aacaggagag    480
cgcacgaggg agcttccagg gggaaacgcc tggtatcttt atagtcctgt cgggtttcgc    540
cacctctgac ttgagcgtcg atttttgtga tgctcgtcag gggggcggag cctatggaaa    600
cgaattcaga tctcgatccc gcgaaattaa tacgactcac tatagggaga ccacaacggt    660
ttccctctag aaataatttt gtttaacttt aagaaggaga tatacatatg agcaaaggtg    720
aagaactgtt taccggcgtt gtgccgattc tggtggaact ggatggcgat gtgaacggtc    780
acaaattcag cgtgcgtggt gaaggtgaag gcgatgccac gattggcaaa ctgacgctga    840
aatttatctg caccaccggc aaactgccgg tgccgtggcc gacgctggtg accaccctga    900
cctatggcgt tcagtgtttt agtcgctatc cggatcacat gaaacgtcac gatttctttta    960 aatctgcaat gccggaaggc tatgtgcagg aacgtacgat tagcttttaaa gatgatggca   1020 aatataaaac gcgcgccgtt gtgaaatttg aaggcgatac cctggtgaac cgcattgaac   1080
tgaaaggcac ggattttaaa gaagatggca atatcctggg ccataaactg aatacaact   1140 ttaatagcca taatgtttat attacggcgg ataaacagaa aaatggcatc aaagcgaatt   1200 ttacccgttcg ccataacgtt gaagatggca gtgtgcagct ggcagatcat tatcagcaga   1260
ataccccgat tggtgatggt ccggtgctgc tgccggataa tcattatctg agcacgcaga   1320
ccgttctgtc taaagatccg aacgaaaaag gcacgcggga ccacatggtt ctgcacgaat   1380
atgtgaatgc ggcaggtatt acgtggaagcc atccgcagtt cgaaaaataa gtcgaccggc   1440
tgctaacaaa gcccgaaagg aagctgagtt ggctgctgcc accgctgagc aataactagc   1500
ataacccctt ggggcctcta acgggtctct gaggggtttt tgctgaaagg ccaattctga   1560
ttagaaaaac tcatcgagca tcaaatgaaa ctgcaattta ttcatatcag gattatcaat   1620
accatatttt tgaaaagcc gtttctgtaa tgaaggagaa aactcaccga ggcagttcca   1680
taggatggca agatcctggt atcggtctgc gattccgact cgtccaacat caatacaacc   1740
tattaatttc ccctcgtcaa aaataaggtt atcaagtgag aaatcaccat gagtgacgac   1800
tgaatccggt gagaatggca aaagcttatg catttctttc cagacttgtt caacaggcca   1860
gccattacgc tcgtcatcaa aatcactcgc atcaaccaaa ccgttattca ttcgtgattg   1920
cgcctgagcg agacgaaata cgcgatcgct gttaaaagga caattacaaa caggaatcga   1980
atgcaaccgg cgcaggaaca ctgccagcgc atcaacaata ttttcacctg aatcaggata   2040
ttcttctaat acctggaatg ctgttttccc ggggatcgca gtggtgagta accatgcatc   2100
atcaggagta cggataaaat gcttgatggt cggaagaggc ataaattccg tcagccagtt   2160
tagtctgacc atctcatctg taacatcatt ggcaacgcta cctttgccat gtttcagaaa   2220
caactctggc gcatcgggct tcccatacaa tcgatagatt gtcgcacctg attgcccgac   2280
attatcgcga gcccatttat acccatataa atcagcatcc atgttggaat ttaatcgcgg   2340
cttcgagcaa gacgtttccc gttgaatatg gctcataaca ccccttgtat tactgtttat   2400
gtaagcagac agttttattg ttcatgatga tatattttta tcttgtgcaa tgtaacatca   2460
```

```
gagattttga gacacaacgt                                              2480
```

<210> SEQ ID NO 2
<211> LENGTH: 60
<212> TYPE: DNA
<213> ORGANISM: Artificial Sequence
<220> FEATURE:
<223> OTHER INFORMATION: SYNTHETIC OLIGONUCLEOTIDE (P1.1-omega-Kozak-
      sfGFP-f)

<400> SEQUENCE: 2

```
acaaacaaca ttacaattac tatttacaat taaaaaaaat gagcaaaggt gaagaactgt    60
```

<210> SEQ ID NO 3
<211> LENGTH: 39
<212> TYPE: DNA
<213> ORGANISM: Artificial Sequence
<220> FEATURE:
<223> OTHER INFORMATION: SYNTHETIC OLIGONUCLEOTIDE (P1.2-sfGFP-r)

<400> SEQUENCE: 3

```
agcagccgga tctcagttta tttttcgaac tgcggatgg                           39
```

<210> SEQ ID NO 4
<211> LENGTH: 96
<212> TYPE: DNA
<213> ORGANISM: Artificial Sequence
<220> FEATURE:
<223> OTHER INFORMATION: SYNTHETIC OLIGONUCLEOTIDE (P2.1-T7-omega-f)

<400> SEQUENCE: 4

```
ccgcgaaatt aatacgactc actataggga gtattttac aacaattacc aacaacaaca    60
aacaacaaac aacattacaa ttactattta caatta                             96
```

<210> SEQ ID NO 5
<211> LENGTH: 70
<212> TYPE: DNA
<213> ORGANISM: Artificial Sequence
<220> FEATURE:
<223> OTHER INFORMATION: SYNTHETIC OLIGONUCLEOTIDE (P2.2PolyA50r)

<400> SEQUENCE: 5

```
tttttttttt tttttttttt tttttttttt tttttttttt tttttttttt gttagcagcc    60
ggatctcagt                                                          70
```

<210> SEQ ID NO 6
<211> LENGTH: 895
<212> TYPE: DNA
<213> ORGANISM: Artificial Sequence
<220> FEATURE:
<223> OTHER INFORMATION: SYNTHETIC DNA (T7-Omega-Kozak-sfGFP-PolyA50)

<400> SEQUENCE: 6

```
ccgcgaaatt aatacgactc actataggga gtattttac aacaattacc aacaacaaca    60
aacaacaaac aacattacaa ttactattta caattaaaaa aaatgagcaa aggtgaagaa   120
ctgtttaccg gcgttgtgcc gattctggtg gaactggatg gcgatgtgaa cggtcacaaa   180
ttcagcgtgc gtggtgaagg tgaaggcgat gccacgattg gcaaactgac gctgaaattt   240
atctgcacca ccggcaaact gccggtgccg tggccgacgc tggtgaccac cctgacctat   300
ggcgttcagt gttttagtcg ctatccggat cacatgaaac gtcacgattt ctttaaatct   360
gcaatgccgg aaggctatgt gcaggaacgt acgattagct ttaaagatga tggcaaatat   420
```

```
aaaacgcgcg ccgttgtgaa atttgaaggc gataccctgg tgaaccgcat tgaactgaaa        480
ggcacggatt ttaaagaaga tggcaatatc ctgggccata aactggaata caactttaat        540
agccataatg tttatattac ggcggataaa cagaaaaatg gcatcaaagc gaattttacc        600
gttcgccata acgttgaaga tggcagtgtg cagctggcag atcattatca gcagaatacc        660
ccgattggtg atggtccggt gctgctgccg gataatcatt atctgagcac gcagaccgtt        720
ctgtctaaag atccgaacga aaaaggcacg cgggaccaca tggttctgca cgaatatgtg        780
aatgcggcag gtattacgtg gagccatccg cagttcgaaa aataaactga gatccggctg        840
ctaacaaaaa aaaaaaaaaa aaaaaaaaaa aaaaaaaaaa aaaaaaaaaa aaaaa             895
```

SUBSTRATE REPLENISHMENT AND BYPRODUCT REMOVAL IMPROVE YEAST CELL-FREE PROTEIN SYNTHESIS

CROSS-REFERENCE TO RELATED APPLICATIONS

This application claims benefit of priority under 35 U.S.C. 119 to U.S. provisional patent application Ser. No. 61/953,275, filed Mar. 14, 2014, and entitled "Substrate Replenishment and Byproduct Removal Improve Yeast Cell-Free Protein Synthesis," the content of which is herein incorporated by reference in its entirety.

STATEMENT OF GOVERNMENT INTEREST

This invention was made with government support under N66001-13-C-4024 awarded by the Space and Naval Warfare Systems Center (DARPA) (subcontract number P010152319 from Leidos, Inc.). The government has certain rights in the invention.

SEQUENCE LISTING

The instant application contains a Sequence Listing that has been submitted in ASCII format via EFS-Web and is hereby incorporated by reference in its entirety. Said ASCII copy, created on Feb. 25, 2015, is named NWN01-083-US_ST25.txt, and is 6,109 bytes in size.

FIELD

The present disclosure relates to methods for improving yeast cell-free protein synthesis.

BACKGROUND

In vitro-directed protein synthesis has an increasingly important role in producing proteins on an industrial scale and for next generation therapeutics. Cell-free protein synthesis (CFPS) has emerged as one strategy for cost-effective and scalable protein production. *Escherichia coli* extract-based CFPS is recognized as a promising technology for protein synthesis in vitro. In vivo eukaryotic protein expression systems are widely used and have shown advantages for producing recombinant proteins that are difficult to actively express in *E. coli*, and similar advantages have been realized with eukaryotic cell-free systems. Similar o the *E. coli* extract platform, *Saccharomyces cerevisiae* benefits from cost-effective microbial fermentation, inexpensive and robust lysate preparation, as well as detailed knowledge from its use as an established protein production platform and model organism.

Yet all eukaryotic CFPS systems currently suffer from lower product yields, expensive reagents, smaller reaction scales, and laborious extract preparation procedures. For example, Hodgman R. Jewett (2013) reported active firefly luciferase yields plateau at about 7.7±0.5 µg-mL$^{-1}$ in 2 h yeast CFPS batch reactions (Hodgman, C. E. and Jewett, M. C., "Optimized extract preparation methods and reaction conditions for improved yeast cell-free protein synthesis. *Biotechnol. Bioeng.* 2013, 110:2643-2654). Although protein synthesis ceased after 2 h in this platform, the reaction's termination did not appear to be caused by a limitation of the catalytic potential of the extract itself, as demonstrated through "pre-incubation" experiments.

The underlying cause(s) of reaction termination for yeast CFPS batch reactions is not understood. Providing a rationale to understand the cause(s) for reaction termination would enable strategies to optimize yeast CFPS batch reaction yields.

BRIEF SUMMARY

In a first aspect, a method is provided for calibrating a cell-free protein synthesis reaction for optimal activity. The method includes the steps of providing an extract competent for cell-free protein synthesis (CFPS); performing cell-free protein synthesis with the extract; measuring a first reaction end-point where in vitro protein synthesis plateaus; measuring a second reaction end-point where Energy Charge of the extract declines to a level in a range from about 0.40 to about 0.80 of Energy Charge of a control extract; and adjusting Energy Charge of the extract to a level in a range from about 0.80 to about 1.0 of the control extract.

In a second aspect, a kit is provided for calibrating a cell-free protein synthesis reaction for optimal activity. The kit includes: an expression template comprising SEQ ID NO:6; a phage T7 DNA polymerase; and an exogenous energy source for adjusting Energy Charge of the cell-free protein synthesis reaction.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

DETAILED DESCRIPTION

Figure 1A:
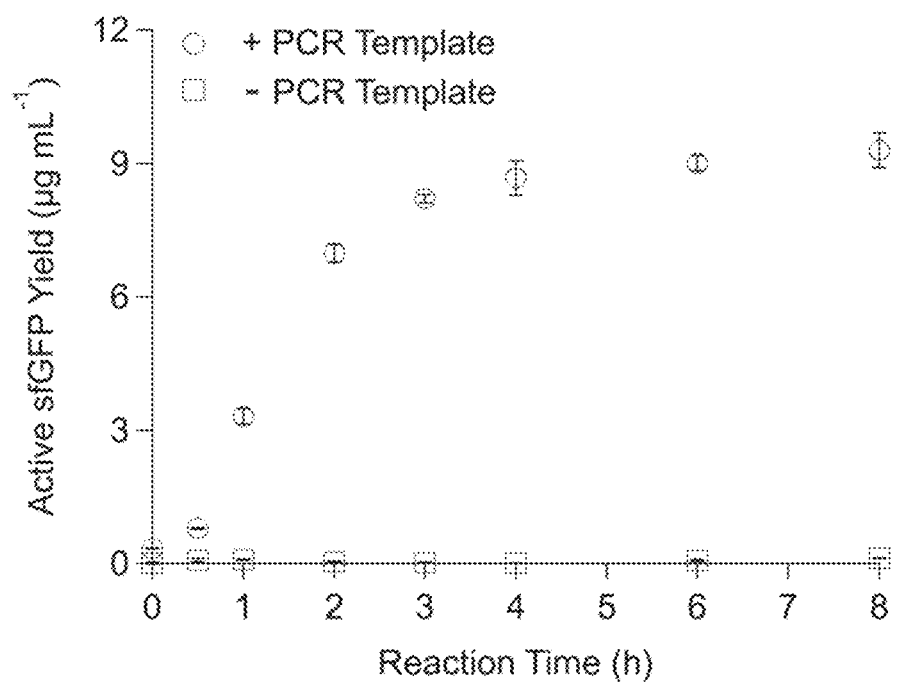
FIG. 1A depicts time course analysis of protein yield for a batch yeast CFPS reaction, wherein active sfGFP synthesis is shown over the course of a standard batch reaction incubated at 21° C. Fifteen microliter batch reactions were prepared in separate 1.5 mL tubes and sampled for active sfGFP yield at the appropriate time points and measured using fluorescence intensity. Reactions were supplied with (circles) or without (squares) sfGFP-encoding PCR template (SEQ ID NO:6). Values show means with error bars representing the standard deviations of three independent experiments.

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Glossary of Terms and Definitions

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Ranges recited herein include the defined boundary numerical values as well as sub-ranges encompassing any non-recited numerical values within the recited range. For example, a range from about 0.01 mM to about 10.0 mM includes both 0.01 mM and 10.0 mM. Non-recited numerical values within this exemplary recited range also contemplated include, for example, 0.05 mM, 0.10 mM, 0.20 mM, 0.51 mM, 1.0 mM, 1.75 mM, 2.5 mM 5.0 mM, 6.0 mM, 7.5 mM, 8.0 mM, 9.0 mM, and 9.9 mM, among others. Exemplary sub-ranges within this exemplary range include from about 0.01 mM to about 5.0 mM; from about 0.1 mM to about 2.5 mM; and from about 2.0 mM to about 6.0 mM, among others.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target, "target sequence", "target region", and "target nucleic acid," as used herein, are synonymous and refer to a region or sequence of a nucleic acid which is to be amplified, sequenced or detected.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, *Biochemistry,* 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example,

*Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

As used herein, coupled transcription/translation ("Tx/Tl"), refers to the de novo synthesis of both RNA and a sequence defined biopolymer from the same extract. For example, coupled transcription/translation of a given sequence defined biopolymer can arise in an extract containing an expression template and a polymerase capable of generating a translation template from the expression template. Coupled transcription/translation can occur using a cognate expression template and polymerase from the organism used to prepare the extract. Coupled transcription/translation can also occur using exogenously-supplied expression template and polymerase from an orthogonal host organism different from the organism used to prepare the extract. In the case of an extract prepared from a yeast organism, an example of an exogenously-supplied expression template includes a translational open reading frame operably coupled a bacteriophage polymerase-specific promoter and an example of the polymerase from an orthogonal host organism includes the corresponding bacteriophage polymerase.

As used herein, Energy Charge (E.C.) refers to the overall status of energy availability in the system (Eq. 1):

$$E.C. = \frac{[ATP] + \frac{1}{2}[ADP]}{[ATP] + [ADP] + [AMP]}. \tag{1}$$

Energy Charge can be calculated by initially determining the concentrations of ATP, ADP and AMP in the extract as a function of time during Tx/Tl CFPS reaction. The Energy Charge of a control extract not used in a CFPS reaction can be used a reference state for the initial Energy Charge of a CFPS reaction. Alternatively, Energy Charge for a CFPS reaction can be assessed for a given extract prior to performing CFPS reaction with the extract (e.g., before adding a required reaction component, such as an expression template or a required polymerase).

Methods for Calibrating Yeast CFPS Reactions for Optimal Activity

A systematic approach is provided to delineate several considerations responsible for limiting in vitro protein synthesis in the yeas based CFPS reaction platforms. By evaluating biochemical reactions, the inventors determined that one source of early reaction termination results from a cascade of events resulting from loss of available energy sources. A se continuous reaction format can alleviate these limitations to realize a ~70% increase in active protein synthesis and information gained can now be leveraged to improve batch reaction performance. The disclosed methods can be adapted to optimize any CFPS platform of interest.

In a first aspect, a method for calibrating a cell-free protein synthesis reaction for optimal activity is provided. The method includes several steps. The first step includes providing an extract competent for cell-free protein synthesis. A variety of methods exist for preparing an extract competent for cell-free protein synthesis. Preferred methods for extract preparation are disclosed in U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2004/0295492 on Oct. 2, 2014.

A preferred organism source for such an extract includes a eukaryotic organism. A highly preferred organism source for such an extract includes a yeast organism, such as *Saccharomyces cerevisiae* and *Schizosaccharomyces pombe*. A highly preferred source for such an extract is the yeast organism *Saccharomyces cerevisiae*.

The second step of the method includes performing cell-free protein synthesis with the extract. A convenient measure of measuring the Tx/Tl activity of a CFPS platform includes the use of an expression template encoding a sequence defined biopolymer. A preferred sequence defined biopolymer includes reporter proteins whose activity can be measured by a convenient and sensitive means, such as an enzyme activity, intrinsic label activity (for example, fluorescence, luminescence, chemiluminescence or bioluminescence, among others) or affinity for a binding partner (for example, biotin-avidin interaction antibody-antigen interaction, or affinity tag interaction (e.g., $His_6$-Ni interaction)). Exemplary reporter proteins include the superfolder Green Fluorescence Protein (sfGFP), chloramphenicol acetyl transferase (CAT) and Luciferase (LUC), among others. A preferred expression template includes the exemplary reporter gene encoding the reporter protein for sfGFP, as presented as SEQ ID NO:6.

Expression templates include an open reading frame operably coupled to a transcriptional promoter element and optionally to a transcriptional termination element. Optimal expression of a translation template in yeast CFPS platforms can also benefit by inclusion of 5'-untranslated region elements (5'-UTR) and 3'-untranslated region elements (3'-UTR) flanking the sequence defined biopolymer open reading frame.

Exemplary 5'-UTR elements include Internal Ribosome Entry Site (IRES) elements or cap-independent translation enhancer sequences to initiate translation. Such sequence elements can circumvent the need to utilize 5'-capped mRNA templates for efficient protein translation in the CFPS platforms. Certain non-native, viral cap-independent sequences, such as the Ω leader sequence (also referred to herein as "Ω leader," "Ω sequence," "Ω" or "Ωcap-independent translation enhancer"), the 5'-UTR from tobacco etch virus (TEV) and 5'-UTR of Crucifer-infecting tobamovirus (Tbm) can have robust activity when operably coupled as an 5'-UTR element to the sequence defined biopolymer-encoded open reading frame within the expression template. Finally, introduction of Kozak sequence elements in the 5'-UTR can lead to improved translation of expression templates.

Exemplary 3'-UTR elements can include sequences having a 3'-terminal poly(A)$_n$ tail that can interact with Poly (A)-Binding Protein (PABP) to enhance protein synthesis and can promote enhance stability. Exemplary 3'-terminal poly(A)n sequences can range from about 20 to 200 nucleotides in length. Preferred 3'-terminal poly(A)$_n$ sequences in the 3'-UTR have a length from about 50 nucleotides to about 170 nucleotides. A highly preferred 3'-terminal poly(A)$_n$ sequence for inclusion in the 3'-UTR has a length of about 50 nucleotides. Additional 3'-UTR elements can be included, such as 3'-UTRs derived from other sources.

Preferred 5'-UTR and 3'UTR elements for inclusion in expression template design for efficient translation template utilization are disclosed in U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2004/0295492 on Oct. 2, 2014.

The natural abundance of charged tRNAs for specifying different codons varies among organisms. Engineering the sequence defined biopolymer open reading frame to include codons optimized for the abundant naturally-occurring tRNAs of *Saccharomyces cerevisiae* can provide another means for promoting efficient utilization of translation template in yeast CFPS platforms.

An exemplary reporter gene expression template for the second step of the method for performing cell-free protein synthesis with the extract includes SEQ ID NO: 6. This nucleotide sequence, when presented in double-stranded form for Tx/Tl in a CFPS platform, encodes an open reading frame for sfGFP that is operably coupled to a phage T7 promoter element, a Ω sequence and Kozak sequence in the 5'-UTR and a 3'-terminal poly(A)$_{50}$ tract in the 3'-UTR. The activity of sfGFP can be readily measured during the time course of performing Tx/Tl in a CFPS reaction.

CFPS platforms having optimized Tx/Tl activity can also be calibrated by modifying the topology of the expression template that encodes a reporter gene mRNA. The exemplary reporter gene expression template disclosed herein, SEQ ID NO: 6, was designed as a linearized template for run-off in vitro transcription by a phage-specific RNA polymerase (for example, T7 RNAP). Because extract can contains endonucleases that degrade linear DNA templates, it may be preferable to use circular DNA templates. Yet excess transcription beyond the desired mRNA gene without termination can consume substrates and lowers transcriptional efficiency. The additional 3' bases found in mRNA run-off transcripts can also interfere with mRNA activity as a translation template.

Accordingly, the 3' end of mRNA-encoding genes can be modified preferably to improve mRNA processing and transcriptional efficiency in the CFPS platforms. Where a phage-specific promoter sequence is used to direct transcription of mRNA-encoding genes, the corresponding phage-specific termination sequence can be used to direct termination of mRNA transcription from circular transcription templates. Examples of suitable phage-specific promoter and termination sequences include those from phages T3, T7 and SP6. A set of highly preferred promoter and termination sequences for controlling mRNA transcription units are those from phage T7.

In addition to the inclusion of phage-specific termination sequences, ribozyme-mediated cleavage motifs can be included at the 3'-ends of the mRNA-encoding genes to enable efficient 3'-end formation of mRNA transcripts. Placement of the ribozyme-mediated cleavage motifs upstream of a phage-specific termination sequence enables removal of extraneous 3'-RNA sequences from mRNA transcripts that result from inefficient transcription termination. Though cis- and trans-mediated ribozyme-mediated cleavage motifs can be included for directed 3'-end formation, the use of cis-acting, self-cleaving ribozyme motifs in the rRNA transcription units is preferred for kinetic reasons. Cis-acting, self-cleaving ribozyme motifs are short sequences that can fold into the appropriate active structure during rRNA transcription to promote self-cleavage within the folded ribozyme structure. Examples of cis-acting, self-cleavage ribozyme motifs include the Hepatitis delta virus (HDV) ribozyme and hammerhead ribozyme(s), among others known in the art.

These and other features of expression template design for optimal translation template production are described in International Patent Application No. PCT/US 14/35376 to Michael Jewett et al., entitled IMPROVED METHODS FOR MAKING RIBOSOMES and filed Apr. 24, 2014, and published as International Patent Application Publication No. WO 2014/176469 on Oct. 30, 2014.

The third step of the method includes measuring a first reaction end-point where in vitro protein synthesis plateaus. Using SEQ ID NO:6 as an expression template for Tx/TI in a CFPS reaction, sfGFP expression batch yeast CFPS reaction was sampled by taking aliquots from the reaction over time and measuring sfGFP fluorescence. Referring to FIG. 1A, the synthesis of sfGFP shows a slight lag during the first 0.5 h and then progresses linearly from 0.5 to 2 h at a rate of 4.06±0.15 μg sfGFP h$^{-1}$. Between 2 and 4 h sfGFP synthesis slows and after 4 h minimal additional sfGFP is synthesized.

Figure 1B:
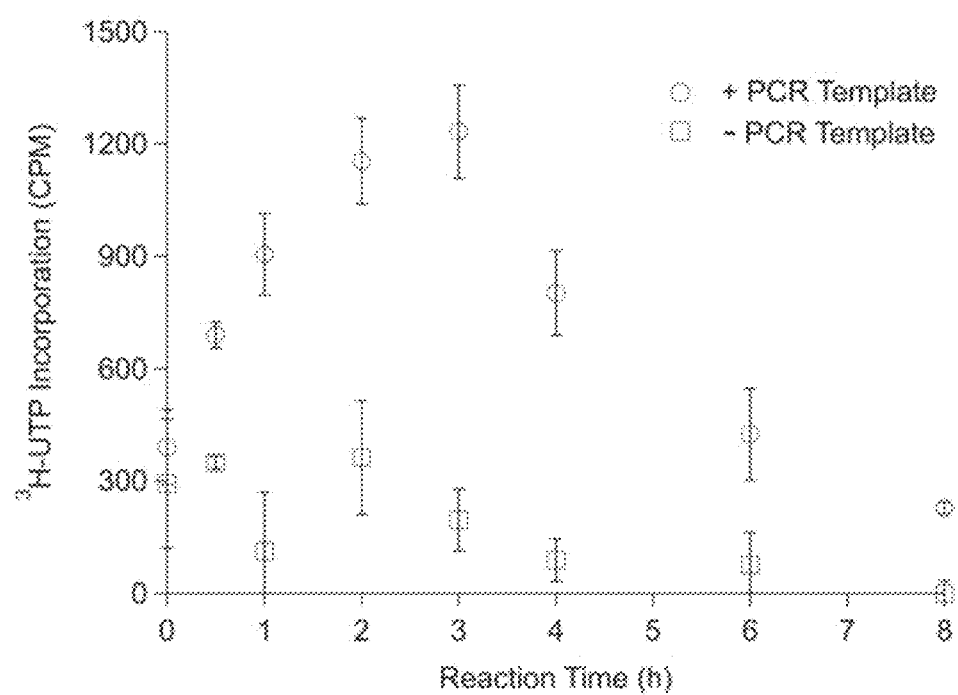
FIG. 1B depicts a time course analysis of mRNA synthesis during a batch yeast CFPS reaction, wherein synthesized mRNA is shown using tritiated UTP incorporation over the course of a standard batch CFPS reaction. Fifteen microliter (15 µL) batch reactions were prepared in separate 1.5 mL tubes supplied with 0.5 µL $^3$H-UTP and sampled at the appropriate time points. The reaction was supplied with and without sfGFP-encoding PCR template. Synthesized mRNA was quantified via scintillation intensity. Values show means with error bars representing the standard deviations of four independent experiments.
Figure 1C:
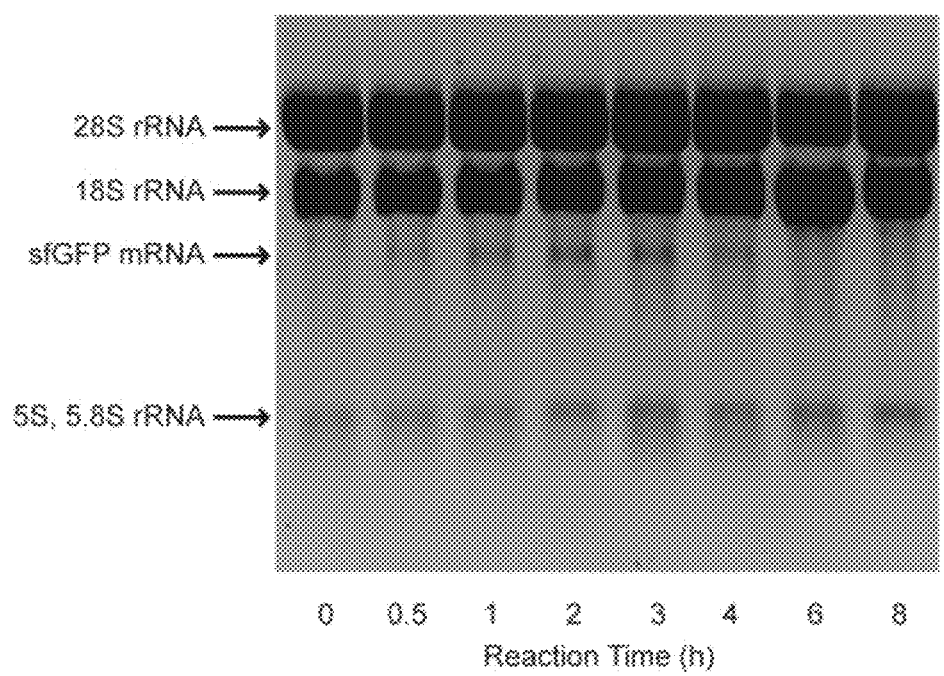
FIG. 1C depicts a time course analysis of mRNA synthesis during a batch yeast CFPS reaction, wherein mRNA was measured via denaturing gel electrophoresis over the course of a standard batch CFPS reaction. Twenty micrograms of purified RNA was added to each lane.

Because sfGFP protein expression in the Tx/Tl CFPS platform depends upon sfGFP-encoded mRNA, the synthesis and degradation of mRNA encoding for sfGFP during the course of the CFPS reaction can be evaluated to determine the role of mRNA fate in the observed sfGFP protein expression profile. FIGS. 1B and 1C show that sfGFP mRNA is synthesized between 0 and 2 h, maintains a relatively constant concentration from 2 to 3 h, and is degraded after 4 h. Because protein synthesis terminates and slows prior to 4 h, the timing of sfGFP mRNA degradation suggests that the mRNA template is not a limiting substrate during batch CFPS reactions.

Figure 2:
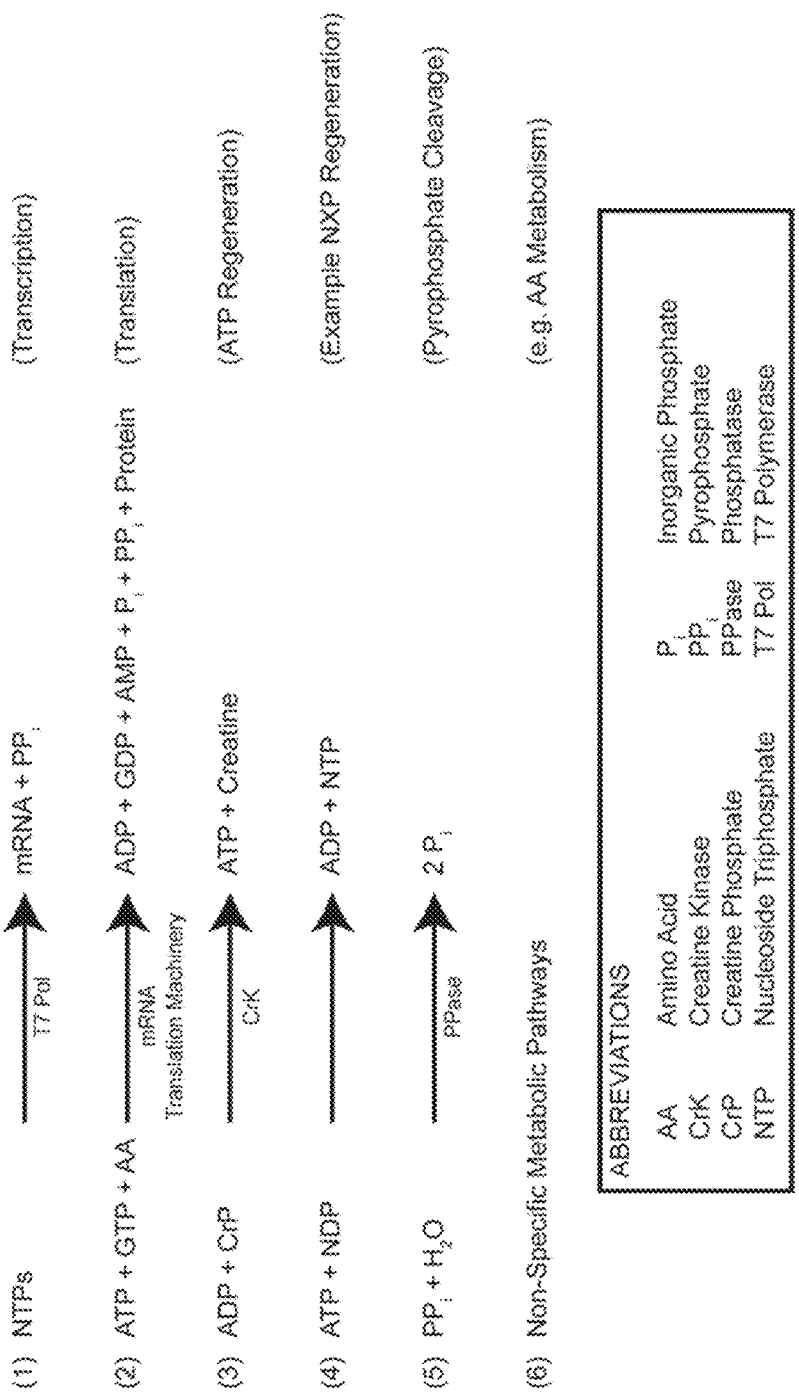
FIG. 2 outlines principal metabolic activities within a yeast cell-free protein synthesis reaction.
Figure 3A:
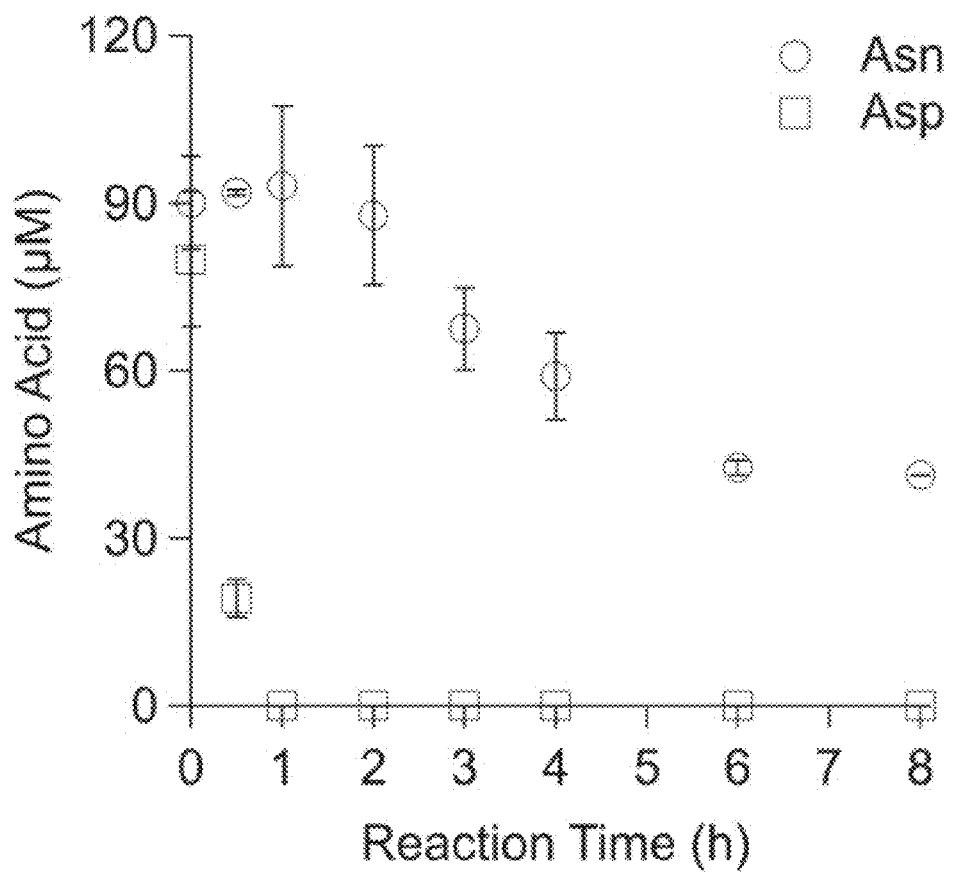
FIG. 3A depicts a time course analysis of select amino acids during a batch yeast CFPS reaction. Fifteen µL batch reactions were prepared in separate 1.5 mL tubes and sampled for active sfGFP yield at the appropriate time points. Concentrations of select amino acid species were measured using HPLC.

In addition to measuring active sfGFP, each sample was assayed for concentration of amino acids, nucleotides, creatine, phosphate, and mRNA in order to characterize the reaction environment during the course of the cell-free reaction. A metabolism diagram that summarizes the major substrate flows within the yeast CFPS reaction is shown in FIG. 2. HPLC analysis of 19 amino acids (glutamate was excluded from the analysis due a concentration of >100 mM), show that aspartic acid and asparagine fall below the exogenously supplied amount (80 µM) within 3 h (FIG. 3A). In fact, no detectable aspartic acid is measured after 1 h reaction time, suggesting a possible amino acid limitation (FIG. 3A).

Figure 3B:
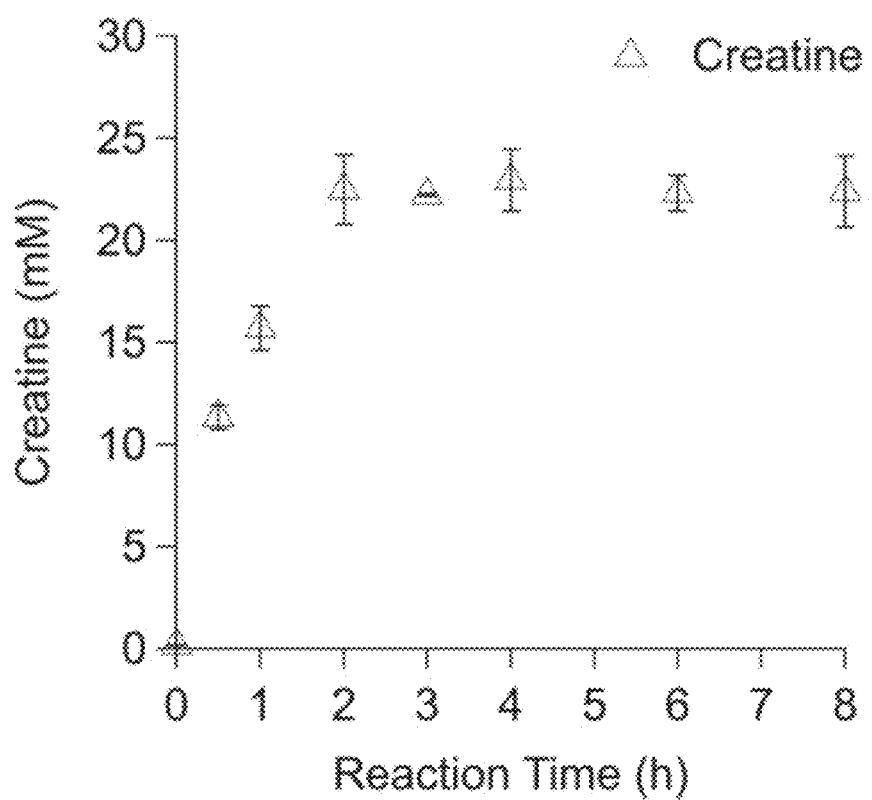
FIG. 3B depicts a time course analysis of creatine measured using a chemical assay during a batch yeast CFPS reaction. Fifteen µL batch reactions were prepared in separate 1.5 mL tubes and sampled for active sfGFP yield at the appropriate time points.

Consumption of creatine phosphate, the secondary energy substrate was measured. Because creatine is not part of a natural biosynthetic pathway in yeast, consumption of creatine phosphate can be measured by measuring the synthesis of creatine (FIG. 3B). A plateau in creatine synthesis occurs after 2 h, which implies the creatine phosphate supply has been exhausted. Once creatine phosphate has been depleted, it is reasonable to assume that ATP can no longer be regenerated (i.e., owing to the use of creatine phosphate as a secondary energy source to form ATP; see details herein).

Figure 3C:
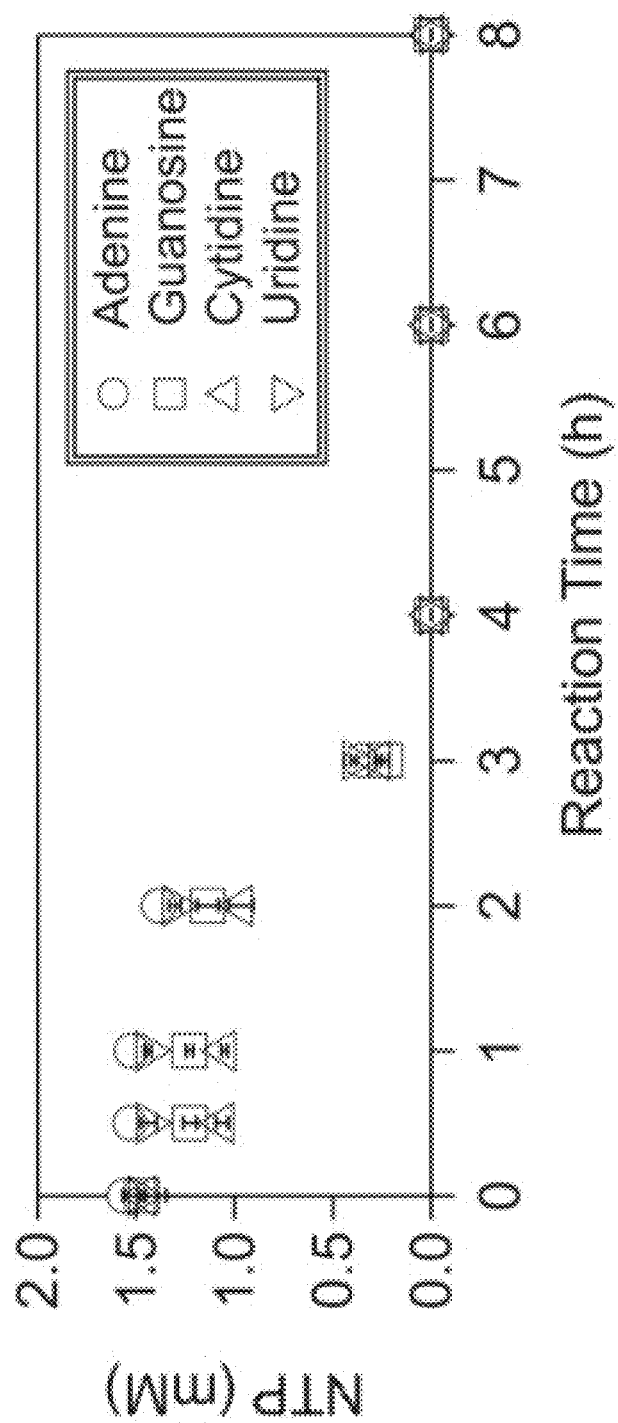
FIG. 3C depicts a time course analysis of nucleoside triphosphate concentrations measured by HPLC during a batch yeast CFPS reaction. Fifteen µL batch reactions were prepared in separate 1.5 mL tubes and sampled for active sfGFP yield at the appropriate tune points.
Figure 3D:
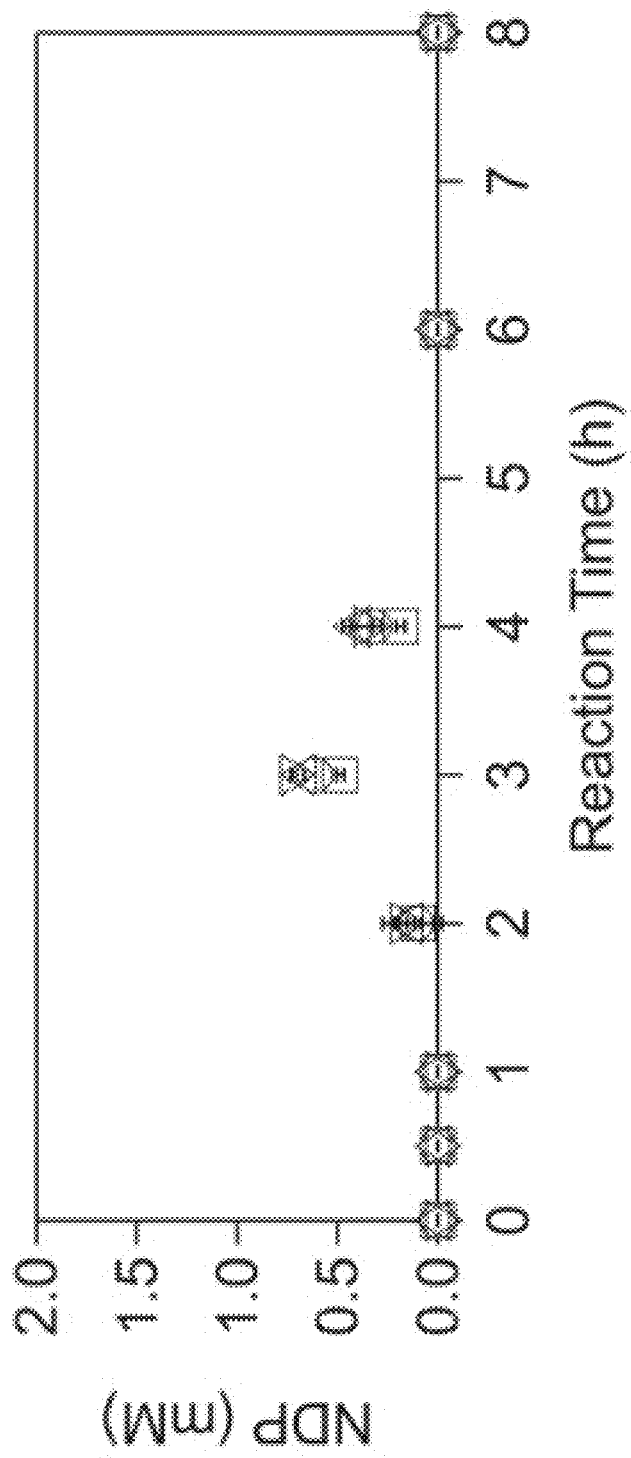
FIG. 3D depicts a time course analysis of diphosphate concentrations measured by HPLC during a batch yeast CFPS reaction. Fifteen microliter (15 µL) batch reactions were prepared in separate 1.5 mL tubes and sampled for active sfGFP yield at the appropriate me points.
Figure 3E:
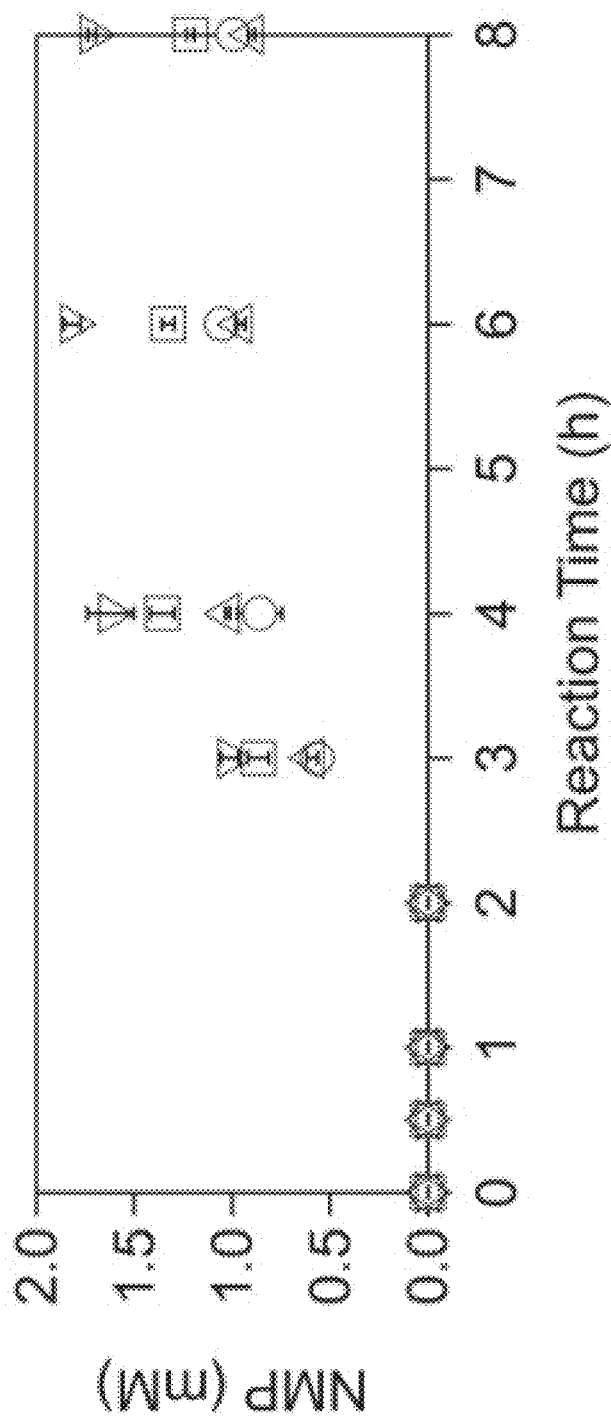
FIG. 3E depicts a time course analysis of monophosphate concentrations measured by HPLC during a batch yeast CFPS reaction. Values show means with error bars representing the standard deviations of data pooled from three independent experiments. Fifteen microliter (15 µL) batch reactions were prepared in separate 1.5 mL tubes and sampled for active sfGFP yield at the appropriate time points.

Quantitative HPLC analysis of the nucleotide pool also shows fluctuation of each species over time. Nucleoside triphosphate (NTP) concentrations stay relatively stable around 1.5 mM each for the first 2 h of the reaction (FIG. 3C). This timing corresponds with the exhaustion of the creatine phosphate supply. As NTPs are consumed, nucleoside diphosphates (NDPs) and nucleoside monophosphates (NMPs) are accumulated sequentially (FIGS. 3D and 3E). NDPs do not accumulate above 0.75 mM each and are quickly converted to their monophosphate form, with the concentration of NMPs stabilizing shortly after 4 h. Without the claimed subject matter being bound to any particular theory, the exhaustion of NTP supply between 2 and 4 h of the reaction would account for the limited transcription of new sfGFP-encoded mRNA observed during this phase of the reaction (see FIGS. 1B and 1C).

Figure 4:
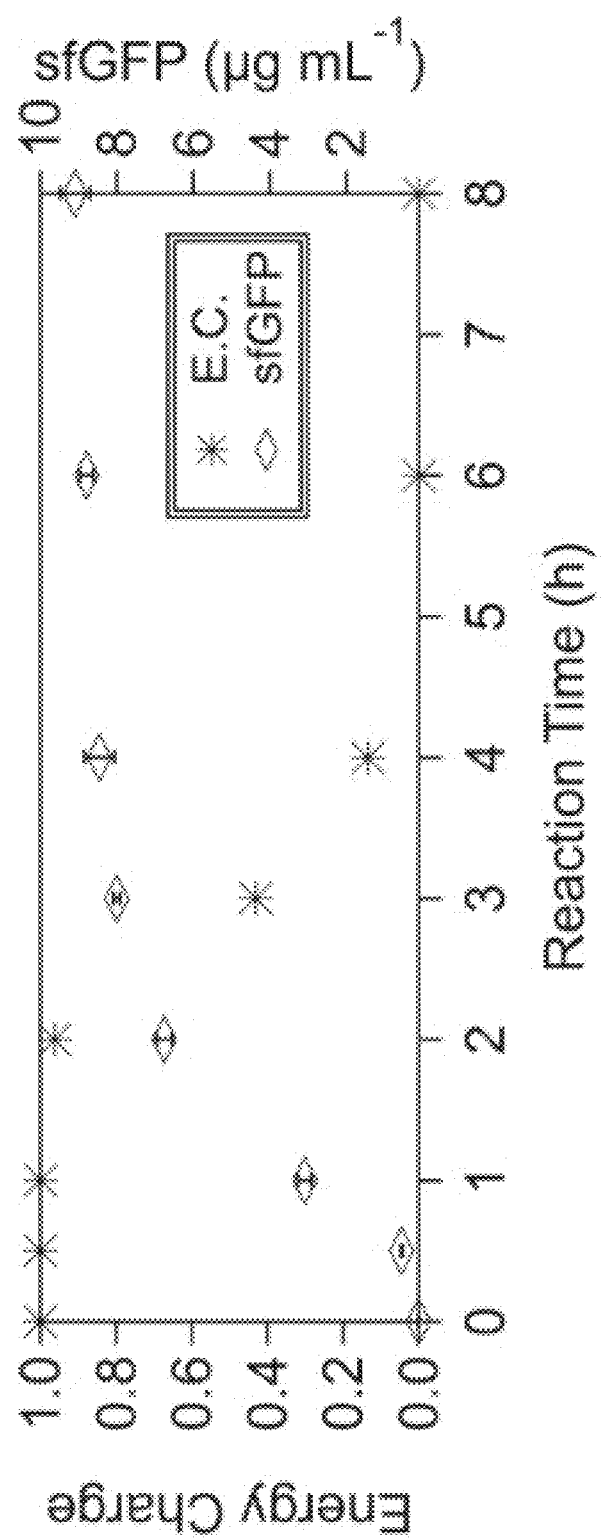
FIG. 4 depicts a time course analysis of Energy charge (E.C.; left axis) and sfGFP (right axis) are plotted against the reaction time. sfGFP yields were measured using fluorescence intensity. Fifteen µL batch reactions were prepared in separate 1.5 mL tubes and sampled for active sfGFP yield at the appropriate tune points.

The fourth step of the method includes measuring a second reaction end-point where Energy Charge (E.C.) of the extract declines to a level in a range from about 0.40 to about 0.80 of Energy Charge of a control extract. Evaluating Energy Charge (E.C.) allows one to hypothesize when energy in the system becomes limiting (Atkinson, D. E., "Energy charge of the adenylate pool as a regulatory parameter. Interaction with feedback modifiers."*Biochemistry* 1968, 7:4030-4034). It has been reported that in vivo E.C. measurements below 0.8 indicate an energy limitation (Chapman, A. G., Fall, L., Atkinson, D. E., "Adenylate energy charge in *Escherichia coli* during growth and starvation." *J. Bacteriol.* 1971, 108:1072-1086). This E.C. threshold is reached in the batch yeast CFPS reaction between 2 and 3 h (FIG. 4).

Fed-Batch Yeast CFPS Reactions: Evaluation of Limiting Substrates for Optimizing CFPS Reaction Performance Fed-batch yeast CFPS reactions were performed to determine whether sfGFP expression in Tx/Tl batch CFPS reactions could be restored with limiting substrate supplements. As shown in FIGS. 3A and 3B, aspartate and creatine phosphate represented potentially limiting substrates and candidates for addition to the fed-batch yeast CFPS reactions. The feed times of 0.5, 1.0, and 1.5 h were chosen based on the time of depletion of aspartic acid (FIG. 3A) and the consumption of creatine phosphate (FIG. 3B). Aspartic acid and creatine phosphate additions were performed individually at 0.5×, 1.0×, and 1.5× the initial concentrations and combined at 1.0× initial concentration. Neither feed time nor feed supplement affected active sfGFP yield (not shown)

The lack of any positive effects on protein synthesis from the fed-batch reactions indicates that substrate depletion is not the only cause of reaction termination. Inorganic phosphate has been previously characterized as a toxic molecule byproduct during CFPS reactions because it sequesters magnesium (Kim, D.-M., Swartz, J. R., "Prolonging cell-free protein synthesis by selective reagent additions," *Biotechnol. Prog.* 2000, 16:385-390). Furthermore, phosphate accumulation during CFPS would be expected with creatine phosphate used as a secondary energy source. Here, a phosphate is donated from creatine phosphate to ADP to regenerate ATP. However, once the phosphate bond is cleaved from an ATP-dependent reaction, the phosphate is unable to be recycled and thus accumulates in the system.

The fifth step of the method includes adjusting Energy Charge of the extract to a level in a range from about 0.80 to about 1.0 of the control extract. A number of energy sources can be used to accomplish this adjustment. ATP as a primary energy source can be used for adjusting Energy Charge of the extract to within the aforementioned range. ATP is an expensive energy source, which renders the adjusting Energy Charge step with ATP very costly. Secondary energy sources suitable for adjusting Energy Charge include creatine phosphate. A preferred secondary energy source suitable for adjusting Energy Charge include a phosphate-free energy source in combination with a phosphate source. Exemplary phosphate-free energy sources include glucose, starch and dextran. Exemplary phosphate sources include exogenous phosphate sources, such as potassium phosphate, magnesium phosphate and ammonium phosphate. Further improvements for adjusting Energy Charge include adding to the extract a combination of a phosphate-free energy source, a phosphate source and an appropriate amount of cAMP (e.g., in the range from about 0.05 mM to about 5.0 mM). These secondary energy sources are described in U.S. patent application Ser. No. 62/098,578 to Michael C. Jewett, entitled METHODS FOR ACTIVATING NATURAL ENERGY METABOLISM FOR IMPROVING YEAST CELL-FREE PROTEIN SYNTHESIS and filed Dec. 31, 2014.

The timing for adjusting Energy Charge is preferably effected before CFPS reaction rates decline, thereby resulting in maximal protein synthesis yields plateauing. Without the claimed subject matter being bound by any particular theory, the rational for this timing decision is that restarting protein synthesis may be subject to a kinetic delay similar to that observed for initiating protein synthesis in a CFPS reaction (see FIG. 1B). In one respect, the adjusting step includes adjusting Energy Charge before a time selected from the first reaction end-point and second reaction end-point. In another respect, performing cell-free protein synthesis with the extract includes performing a coupled transcription/translation reaction. In this respect, the coupled transcription/translation reaction includes an expression template such as SEQ ID NO:6 and a polymerase such as phage T7 DNA polymerase. In particular, the polymerase selected in the foregoing respect should be orthogonal to the promoter operably coupled to the expression template.

Removal of Toxic Metabolic Byproducts can Improve CFPS Reaction Performance.

Figure 5A:
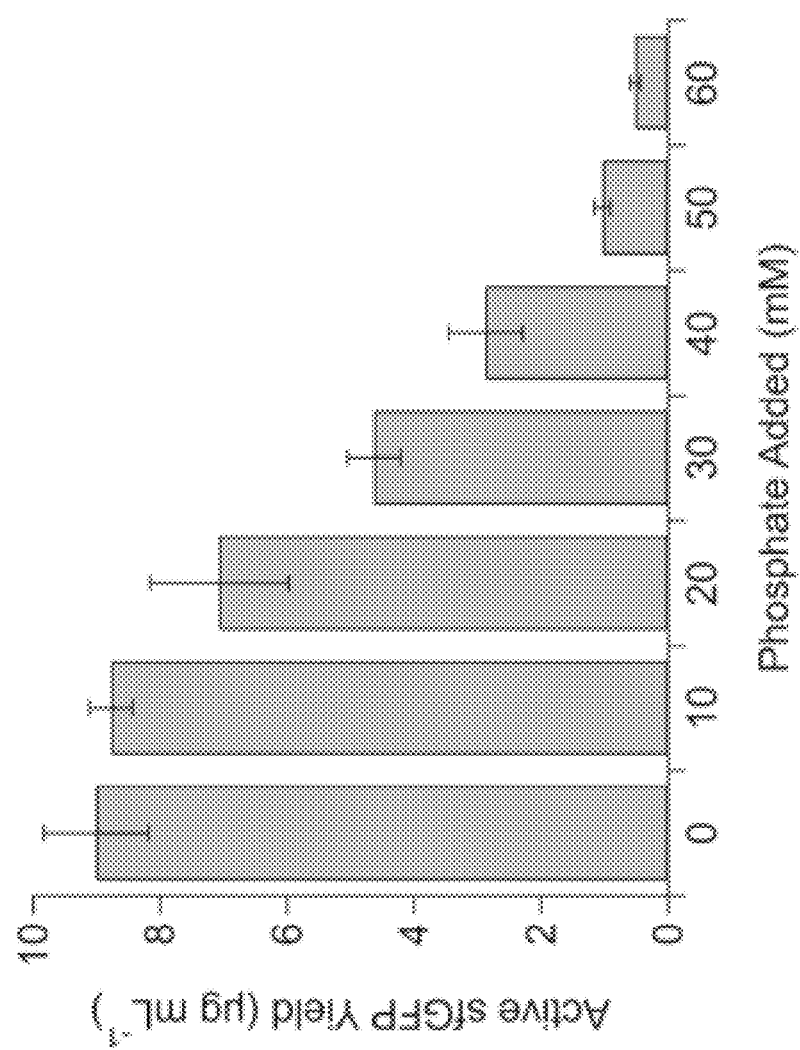
FIG. 5A depicts the effect of additional phosphate being added to 15 µL batch reactions at time 0 h in the form of potassium phosphate (pH 7.4), ranging from 0 to 60 mM. The additional potassium was offset by a reduction in potassium glutamate added to the reaction.
Figure 5B:
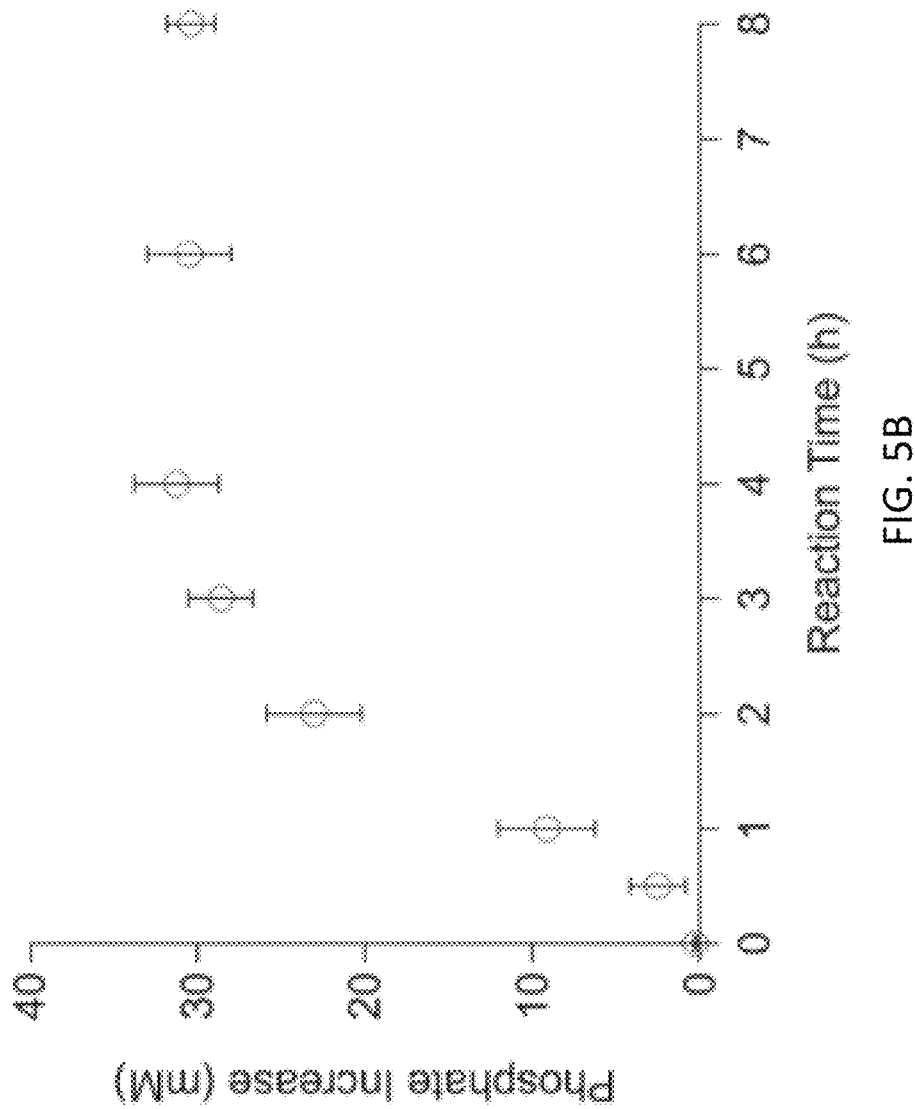
FIG. 5B depicts phosphate concentration being measured using a enzymatic assay and analyzed over the course of a standard batch CFPS reaction. Values show means with error bars representing the standard deviations of data pooled from three independent experiments.

To evaluate the effect of phosphate on the system, potassium phosphate was added to the system at the start of the reaction in known concentrations (FIG. 5A). With as little as 30 mM additional phosphate added to the system, sfGFP production is reduced by 50%. Similarly, the accumulation of additional 30 mM phosphate is observed within 3 h of the reaction (FIG. 5B). To offset inorganic phosphate accumulation, one established strategy is to include magnesium in a fed-batch reaction [Kim, D.-M., Swartz, J. R., "Prolonging cell-free protein synthesis by selective reagent additions," *Biotechnol. Prog.* 2000, 16:385-390]. However, this showed no benefit in overall yield (not shown). Without the claimed subject matter being limited to any particular theory, despite the addition of magnesium and limiting substrates, inorganic phosphate accumulation remains a likely factor preventing he anticipated increase with respect o protein production in fed-batch reactions.

Figure 6A:
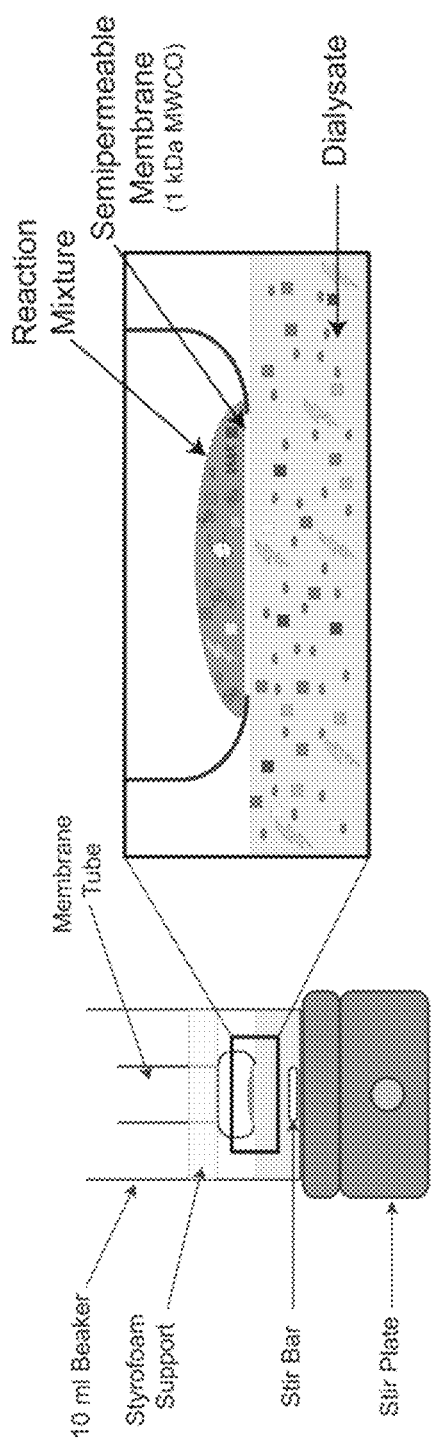
FIG. 6A depicts a schematic of the experimental set-up for the semi-continuous exchange reactions.
Figure 6B:
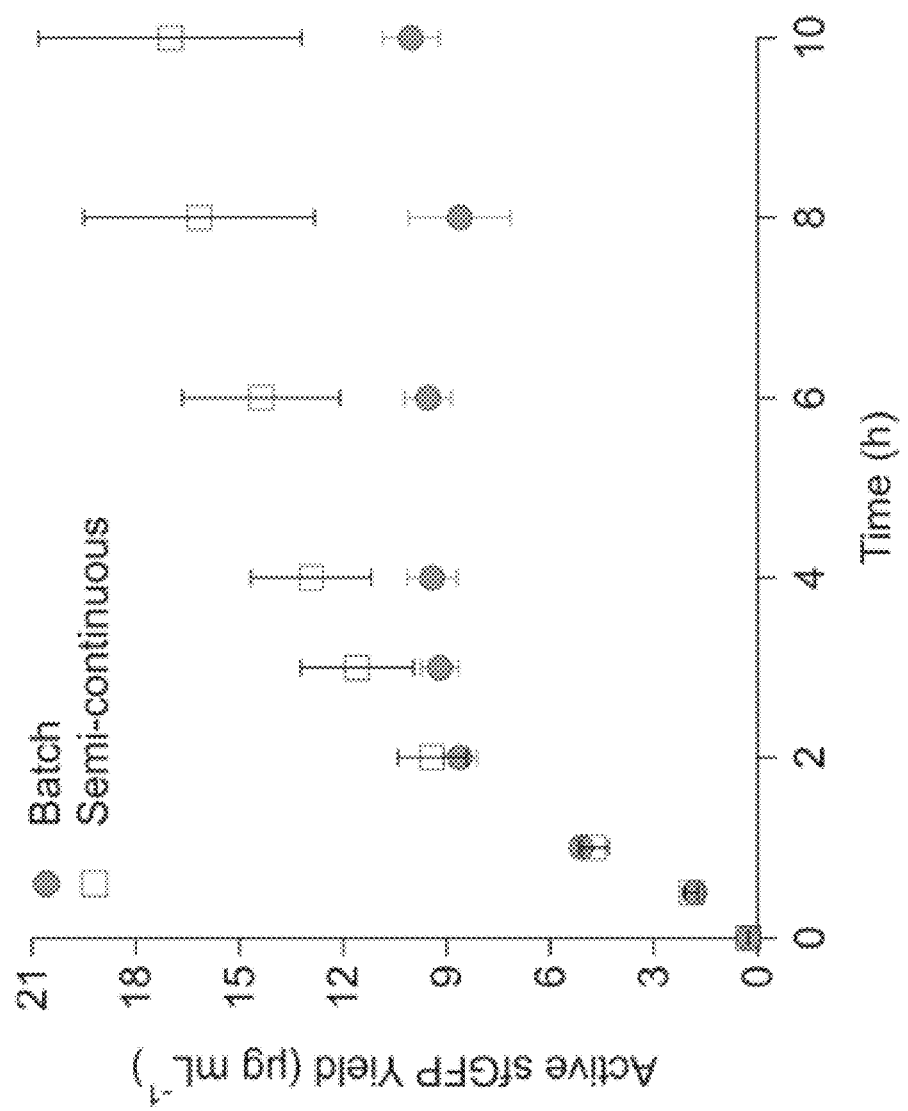
FIG. 6B depicts sfGFP synthesis shown over the course of a semi-continuous CFPS reaction. Reactions were sampled at the appropriate time points to measure active sfGFP yield using fluorescence intensity.
Figure 6C:
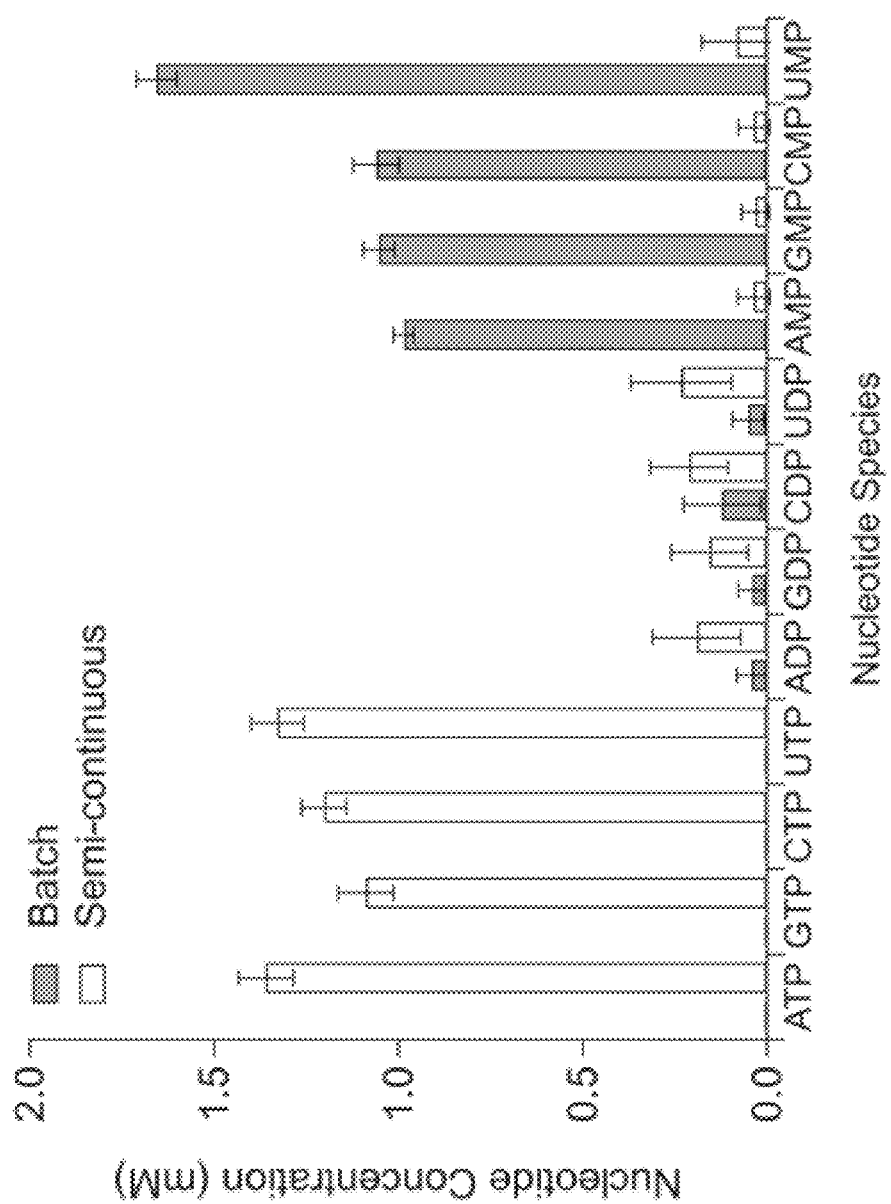
FIG. 6C depicts endpoint nucleotide measurements after a 10 h semi-continuous reaction using HPLC.
Figure 6D:
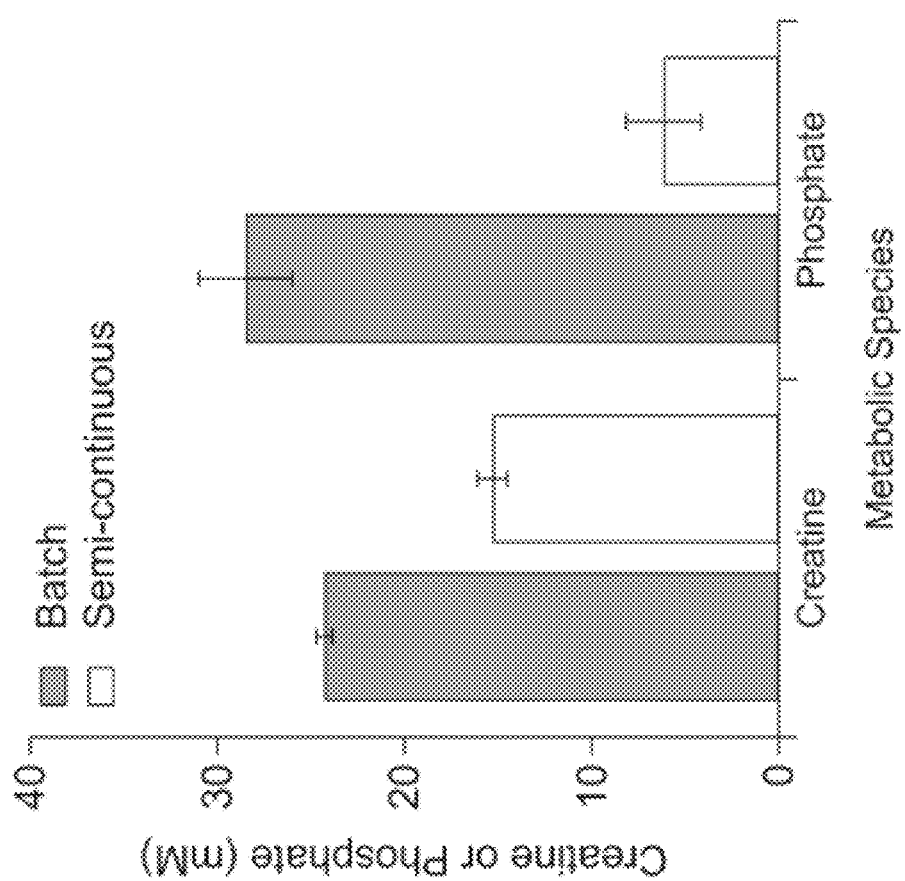
FIG. 6D depicts endpoint creatine and phosphate measurements after a 10 h semi-continuous reaction using chemical assays.
Figure 6E:
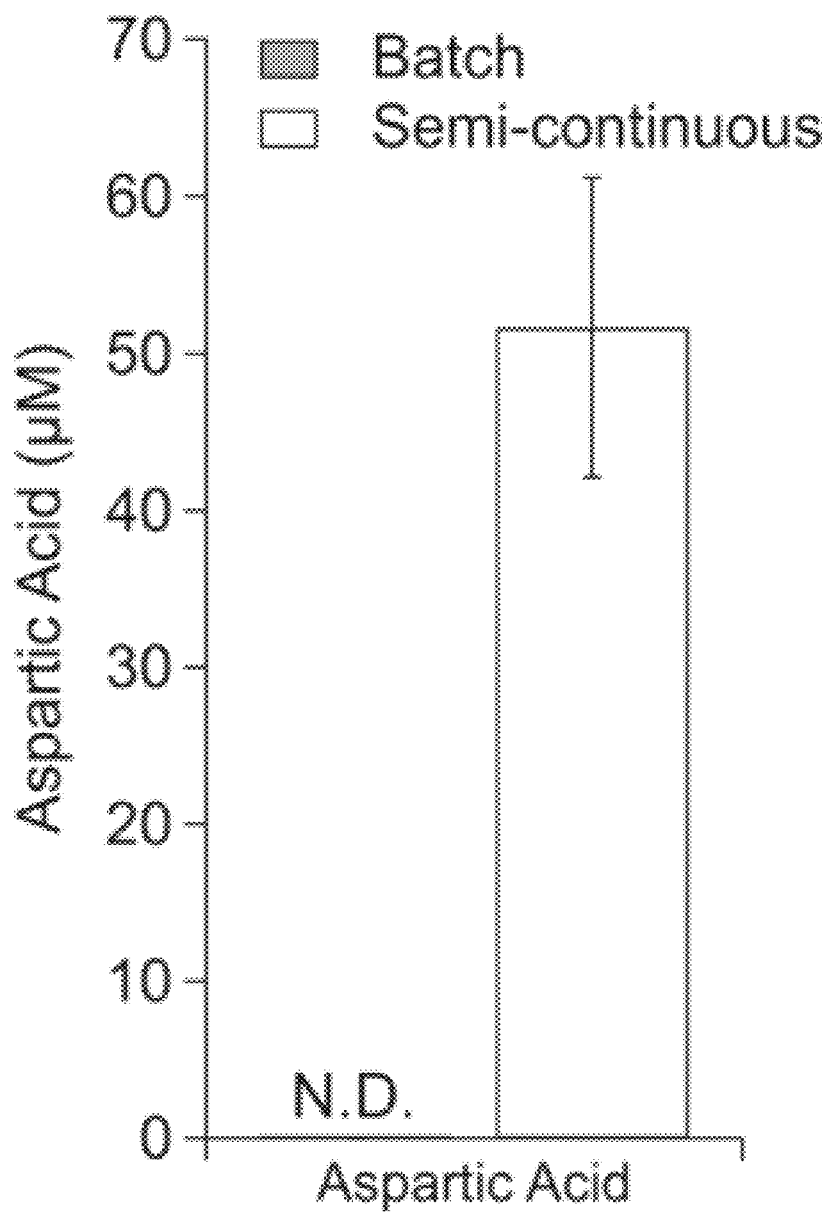
FIG. 6E depicts endpoint aspartic acid measurements after a 10 h semi-continuous reaction using HPLC. N.D., none detected. Values in FIGS. 6B-E show means with error bars representing the standard deviations of data pooled from at least three independent experiments, While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

To allow for limiting substrate replenishment and byproduct removal, a semi-continuous exchange method was used, as illustrated in FIG. 6A. The 1 kDa molecular weight cut off (MWCO) semipermeable membrane allows for passive diffusion of small molecules between the reaction mixture inside the membrane tube and the dialysate, while keeping the enzymes and translation machinery contained within the reaction. While these experiments were performed for 100 µL reaction volumes, the increase in reaction volume has no effect on sfGFP yield (not shown). When samples of the batch and semi-continuous reactions at time points of 0, 0.5, 1, 2, 3, 4, 6, 8, and 10 h were assayed for active sfGFP (FIG. 6B), the semi-continuous method led to a 70% improvement in protein synthesis yields over the batch reaction, producing 17.0±3.8 ig mL$^{-1}$. In addition, the NTP measurements clearly show that, compared to the batch reaction where NTPs are completely depleted by 4 h, the semi-continuous method is able to sustain the NTP pool above 1 mM up to 10 h (FIG. 6C). Similarly, FIG. 6D shows that the semi-continuous reaction maintains reduced concentrations of both creatine and phosphate compared to the batch reaction. Finally, FIG. 6E also shows that the aspartic acid is no longer limiting in the se continuous reaction, despite its depletion in the batch reaction. In addition, other amino acids—excluding arginine, which is synthesized in the semi-continuous reaction—are at the same concentration in the semi-continuous reaction and the dialysate, indicating good diffusion across the membrane (not shown). These results demonstrate that the exchange of small molecules, including limiting substrates and toxic byproducts, does indeed prolong the reaction length, leading to a higher protein yield.

In view of the foregoing, another aspect of the method for calibrating a cell-free protein synthesis reaction for optimal activity further includes the step of removing a toxic metabolic byproduct from the CFPS reaction. In this respect, the toxic metabolic byproduct includes inorganic phosphate. In another respect, the cell-free protein synthesis reaction is selected from a batch CFPS reaction or a semi-continuous CFPS reaction.

In second aspect, a kit for calibrating a cell-free protein synthesis reaction for optimal activity is provided. The kit includes: an expression template comprising SEQ ID NO:6; a phage T7 DNA polymerase; and an exogenous energy source for adjusting Energy Charge of the cell-free protein synthesis reaction.

EXAMPLES

The invention will be more fully understood upon consideration of the following non-limiting examples, which are offered for purposes of illustration, not limitation.

Example 1

Nucleic Acids and sfGFP DNA Template Preparation

Linear DNA template encoding for sfGFP was amplified from the pY71sfGFP plasmid (SEQ ID NO:1). A two-stage polymerase chain reaction (PCR) method was adopted to amplify the sfGFP gene as explained below. The plasmid and primer sequences are provided in Table 1.

TABLE 1

Nucleic acids used for encoding sfGFP amplification products

| Nucleic Acid [SEQ ID NO:_] | Nucleotide Sequence (5' → 3')[1] |
|---|---|
| pY71sfGFP [SEQ ID NO: 1] | GGATCCTGCAGTTGAGATCCTTTTTTTCTGCGCGTAATCTGCTGCT TGCAAACAAAAAAACCACCGCTACCAGCGGTGGTTTGTTTGCCGG ATCAAGAGCTACCAACTCTTTTTCCGAAGGTAACTGGCTTCAGCAG AGCGCAGATACCAAATACTGTCCTTCTAGTGTAGCCGTAGTTAGGC CACCACTTCAAGAACTCTGTAGCACCGCCTACATACCTCGCTCTGC TAATCCTGTTACCAGTGGCTGCTGCCAGTGGCGATAAGTCGTGTC TTACCGGGTTGGACTCAAGACGATAGTTACCGGATAAGGCGCAGC GGTCGGGCTGAACGGGGGGTTCGTGCACACAGCCCAGCTTGGAG CGAACGACCTACACCGAACTGAGATACCTACAGCGTGAGCATTGA GAAAGCGCCACGCTTCCCGAAGGGAGAAAGGCGGACAGGTATCC GGTAAGCGGCAGGGTCGGAACAGGAGAGCGCACGAGGGAGCTTC CAGGGGGAAACGCCTGGTATCTTTATAGTCCTGTCGGGTTTCGCC ACCTCTGACTTGAGCGTCGATTTTTGTGATGCTCGTCAGGGGGGC GGAGCCTATGGAAACGAATTCAGATCTCGATCCCGCGAAATTAATA CGACTCACTATAGGGAGACCACAACGGTTTCCCTCTAGAAATAATT TTGTTTAACTTTAAGAAGGAGATATACATatgagcaaaggtgaagaactgtTT ACCGGCGTTGTGCCGATTCTGGTGGAACTGGATGGCGATGTGAAC GGTCACAAATTCAGCGTGCGTGGTGAAGGTGAAGGCGATGCCAC GATTGGCAAACTGACGCTGAAATTTATCTGCACCACCGGCAAACTG CCGGTGCCGTGGCCGACGCTGGTGACCACCCTGACCTATGGCGT TCAGTGTTTTAGTCGCTATCCGGATCACATGAAACGTCACGATTTC TTTAAATCTGCAATGCCGGAAGGCTATGTGCAGGAACGTACGATTA GCTTTAAAGATGATGGCAAATATAAAACGCGCGCCGTTGTGAAATT TGAAGGCGATACCCTGGTGAACCGCATTGAACTGAAAGGCACGGA TTTTAAAGAAGATGGCAATATCCTGGGCCATAAACTGGAATACAAC TTTAATAGCCATAATGTTTATATTACGGCGGATAAACAGAAAAATGG CATCAAAGCGAATTTTACCGTTCGCCATAACGTTGAAGATGGCAGT GTGCAGCTGGCAGATCATTATCAGCAGAATACCCCGATTGGTGAT GGTCCGGTGCTGCTGCCGGATAATCATTATCTGAGCACGCAGACC GTTCTGTCTAAAGATCCGAACGAAAAAGGCACGCGGGACCACATG |

TABLE 1-continued

Nucleic acids used for encoding sfGFP amplification products

| Nucleic Acid [SEQ ID NO:_] | Nucleotide Sequence (5' → 3')[1] |
|---|---|
| | GTTCTGCACGAATATGTGAATGCGGCAGGTATTACGTGGAGccatcc<br>gcagttcgaaaaataaGTCGACCGGCTGCTAACAAAGCCCGAAAGGAAG<br>CTGAGTTGGCTGCTGCCACCGCTGAGCAATAACTAGCATAACCCC<br>TTGGGGCCTCTAAACGGTCTTGAGGGGTTTTTTGCTGAAAGCCA<br>ATTCTGATTAGAAAAACTCATCGAGCATCAAATGAAACTGCAATTTA<br>TTCATATCAGGATTATCAATACCATATTTTTGAAAAAGCCGTTTCTG<br>TAATGAAGGAGAAAACTCACCGAGGCAGTTCCATAGGATGGCAAG<br>ATCCTGGTATCGGTCTGCGATTCCGACTCGTCCAACATCAATACAA<br>CCTATTAATTTCCCCTCGTCAAAAATAAGGTTATCAAGTGAGAAATC<br>ACCATGAGTGACGACTGAATCCGGTGAGAATGGCAAAAGCTTATG<br>CATTTCTTTCCAGACTTGTTCAACAGGCCAGCCATTACGCTCGTCA<br>TCAAAATCACTCGCATCAACCAAACCGTTATTCATTCGTGATTGCG<br>CCTGAGCGAGACGAAATACGCGATCGCTGTTAAAAGGACAATTAC<br>AAACAGGAATCGAATGCAACCGGCGCAGGAACACTGCCAGCGCAT<br>CAACAATATTTTCACCTGAATCAGGATATTCTTCTAATACCTGGAAT<br>GCTGTTTTCCCGGGGATCGCAGTGGTGAGTAACCATGCATCATCA<br>GGAGTACGGATAAAATGCTTGATGGTCGGAAGAGGCATAAATTCC<br>GTCAGCCAGTTTAGTCTGACCATCTCATCTGTAACATCATTGGCAA<br>CGCTACCTTTGCCATGTTTCAGAAACAACTCTGGCGCATCGGGCTT<br>CCCATACAATCGATAGATTGTCGCACCTGATTGCCCGACATTATCG<br>CGAGCCCATTTATACCCATATAAATCAGCATCCATGTTGGAATTTAA<br>TCGCGGCTTCGAGCAAGACGTTTCCCGTTGAATATGGCTCATAACA<br>CCCCTTGTATTACTGTTTATGTAAGCAGACAGTTTTATTGTTCATGA<br>TGATATATTTTTATCTTGTGCAATGTAACATCAGAGATTTTGAGACA<br>CAACGT |
| P1.1-Ω-Kozak-sfGFP-f [SEQ ID NO: 2] | <u>ACAAACAACATTACAATTACTATTTACAATTA</u>AAAAAA*atgagcaaaggtg*<br>*aagaactgt* |
| P1.2-sfGFP-r [SEQ ID NO: 3] | <u>AGCAGCCGGATCTCAGT</u>ttatttttcgaactgcggatgg |
| P2.1-T7-Ω-f | CCGCGAAATTAATACGACTCACTATAGGGAG<u>TATTTTTACAACAAT</u> |
| [SEQ ID NO: 4] | <u>TACCAACAACAACAAACAACAAACAACATTACAATTACTATTTACAA</u><br><u>TTA</u> |
| P2.2PolyA50r [SEQ ID NO: 5] | TTTTTTTTTTTTTTTTTTTTTTTTTTTTTTTTTTTTTTTTTTTTTTTTTG<br>TT<u>AGCAGCCGGATCTCAGT</u> |
| T7-Ω-Kozak-sfGFP-PolyA50 [SEQ ID NO: 6] | CCGCGAAATTAATACGACTCACTATAGGGAG<u>TATTTTTACAACAAT</u><br><u>TACCAACAACAACAAACAACAAACAACATTACAATTACTATTTACAA</u><br><u>TTA</u>*AAAAAA*atgagcaaaggtgaagaactgtTTACCGGCGTTGTGCCGATTC<br>TGGTGGAACTGGATGGCGATGTGAACGGTCACAAATTCAGCGTGC<br>GTGGTGAAGGTGAAGGCGATGCCACGATTGGCAAACTGACGCTGA<br>AATTTATCTGCACCACCGGCAAACTGCCGGTGCCGTGGCCGACGC<br>TGGTGACCACCCTGACCTATGGCGTTCAGTGTTTTAGTCGCTATCC<br>GGATCACATGAAACGTCACGATTTCTTTAAATCTGCAATGCCG GAA<br>GGCTATGTGCAG GAACGTACGATTAGCTTTAAAGATGATGGCAAAT<br>ATAAAACGCGCGCCGTTGTGAAATTTGAAGGCGATACCCTGGTGA<br>ACCGCATTGAACTGAAAGGCACGGATTTTAAAGAAGATGGCAATAT<br>CCTGGGCCATAAACTGGAATACAACTTTAATAGCCATAATGTTTATA<br>TTACGGCGGATAAACAGAAAAATGGCATCAAAGCGAATTTTACCGT<br>TCGCCATAACGTTGAAGATGGCAGTGTGCAGCTGGCAGATCATTA<br>TCAGCAGAATACCCCGATTGGTGATGGTCCGGTGCTGCTGCCGGA<br>TAATCATTATCTGAGCACGCAGACCGTTCTGTCTAAAGATCCGAAC<br>GAAAAAGGCACGCGGGACCACATGGTTCTGCACGAATATGTGAAT<br>GCGGCAGGTATTACGTGGAGccatccgcagttcgaaaaataa<u>ACTGAGATC</u><br><u>CGGCTGCT</u>AACAAAAAAAAAAAAAAAAAAAAAAAAAAAAAAAAAA<br>AAAAAAAAAAAAAA |

[1]Key: Lower case font: sfGFP gene-specific overlap in SEQ ID NOs: 1-3;
Italics font: *S. cerevisiae* consensus Kozak sequence;
Bold font: T7 Promoter;
Underlined font: Tobacco Mosaic Virus Ω Sequence (contains 5' overlap between PCR1 and PCR2 [SEQ ID NOs: 2 and 4]);
Double-underlined font: 3' overlap between PCR1 and PCR2 [SEQ ID NOs: 3 and 5].

The first PCR stage reaction used SEQ ID NO:1 as the amplification template and SEQ ID NOs: 2 and 3 as PCR primers. In the first PCR stage reaction, sense and anti-sense primers (SEQ ID NOs: 2 and 3, respectively) were designed to anneal to the sfGFP sequence in the pY71sfGFP plasmid (SEQ ID NO:1) and add overlapping regions to each end of the PCR product. The 5' end of the first PCR stage reaction product contained a flanking sequence encoding the canonical yeast Kozak sequence (AAAAAA) and partially encoding the sequence from tobacco mosaic virus. The 3' end of the first PCR stage reaction product contained an additional 17 nt flanking sequence.

The second PCR stage reaction used the first PCR stage reaction product as the amplification template and SEQ ID NOs: 4 and 5 as PCR primers. In the second PCR stage reaction, sense and anti-sense primers (SEQ ID NOs: 4 and 5, respectively) were designed to anneal to the 5' and 3' flanking sequences, respectively, of the first PCR stage reaction product. The 5' region of the full-length PCR product encoded the full sequence (65 nt) as well as the T7 Promoter sequence. The 3' end encoded a 50 nt poly(T) sequence to extend the mRNA with a poly(A)$_{50}$ tail. The resultant second PCR stage reaction product (SEQ ID NO:6) encoded the full-length sfGFP-encoded mRNA, and transcription was assumed to terminate via run-off of the T7 bacteriophage polymerase.

Example 2

Yeast Extract Preparation

Extracts were prepared by the same method developed by Hodgman & Jewett (2013) with fermentation for cellular growth, high-pressure homogenization for cell lysis, and dialysis for buffer exchange. *S. cerevisiae* strain MBS was used as the source strain for extract preparation (Iizuka, N., Najita, L., Franzusoff, A., Sarnow, P., "Cap-dependent and cap-independent translation by internal initiation of mRNAs in cell extracts prepared from *Saccharomyces cerevisiae*." *Mol. Cell. Biol.* 1994, 14:7322-7330).

Example 3

Cell-Free Protein Synthesis Reactions

Experiments with CFPS were done with three different reaction systems: (i) batch reactions; (2) fed-batch reactions; and (3) semi-continuous reactions. Each reaction system is described below.

(1) CFPS Batch Reactions

CFPS batch reactions were carried out according to the method for combined Tx/Tl reactions in Hodgman and Jewett (2013) with the following working concentrations: 22 mM 4-(2-Hydroxyethyl)piperazine-1-ethanesulfonic acid (HEPES)-KOH pH 7.4, 120 mM potassium glutamate, 4.5 mM magnesium glutamate, 1.5 mM each of adenosine triphosphate (ATP), guanosine triphosphate (GTP), cytidine triphosphate (CTP), and uridine triphosphate (UTP), 0.08 mM each of 20 amino acids, 25 mM creatine phosphate, 1.7 mM dithiothreitol (DTT), 1 mM putrescine, 0.5 mM spermidine, 11% v/v glycerol, 0.27 mg mL$^{-1}$ creatine phosphokinase (from rabbit muscle; Sigma-Aldrich, St. Louis, Mo.), 0.027 mg mL$^{-1}$ T7 RNA polymerase (made in house following the protocol developed by Swartz, J. R., Jewett, M. C., Woodrow, K. A., "Cell-free protein synthesis with prokaryotic combined transcription-translation," *Methods Mol. Biol.* 2004, 267:169-182), 6.67 µg·mL$^{-1}$ Ω-sfGFP-A$_{50}$ PCR-amplified DNA, and 50% v/v yeast extract. The concentration of proteins in the yeast extract was 18.2±0.9 mg·mL$^{-1}$, as determined by Bradford Assay using commercially available assay reagents (Bio-Rad, Hercules, Calif.) compared to a bovine serum albumin protein standard. All other reagents were purchased from Sigma-Aldrich unless otherwise noted.

(2) Fed-Batch CFPS Reactions

Fifteen microliter (15 CFPS batch reactions were prepared as described above. At the specified time, the reactions were removed from the incubator, supplied with 1 µL of feeding solution containing the appropriate concentration of the desired substrate(s), mixed with a pipette, and returned to the incubator. All reactions were incubated at 21° C. for 8 h total and assayed using the sfGFP assay.

(3) Semi-Continuous CFPS Reactions

A 10 mL beaker with 2 mL of dialysate was placed on a stir plate with a stir bar. A membrane tube (1 kDa. MWCO Tube-O-Dialyzer; G-Biosciences, St. Louis, Mo.) was placed in the foam support with the membrane cap facing downward in the beaker such that the membrane contacted the surface of the dialysate with minimal submersion. The non-membrane end of the tube was removed for adding the reaction mixture and sampling. The beaker was covered with aluminum foil when not sampling. Initial reaction volumes totaled 100 µL, with the same composition as the batch reactions. The dialysate imitated the final reaction mixture: 37 mM HEPES-KOH pH 7.4, 170 mM potassium glutamate, 5.5 mM magnesium glutamate, 1.5 mM each of ATP, GTP, CTP, and UTP, 0.08 mM each of 20 amino acids, 25 mM creatine phosphate, 1.9 mM DTT, 1 mM putrescine, 0.5 mM spermidine, 11.0% glycerol, 0.05 mM phenylmethanesulfonyl fluoride (PMSF), and 115 mM mannitol. Differences in concentrations between the batch reaction mixture and the dialysate were due to contributions from the lysis buffer in the reaction. The reactions occurred at room temperature (23-24° C.) and were compared to a 100 µL batch reaction occurring under the same conditions. At 0, 0,5, 1, 2, 3, 4, 6, 8, and 10 h of incubation time, 5 µL samples were removed from the batch and semi-continuous reactions, frozen on liquid nitrogen to quench the reaction, and later thawed and assayed concurrently. The remainder of the reaction mixture after 10 h of incubation was saved for small molecule assays and stored at −80° C. until use.

Example 4

Denaturing RNA Gel Electrophoresis

The denaturing RNA gel was prepared with 1.5% agarose containing 2.2 M formaldehyde and 2× GelRed in 1× MOPS Buffer (2 M 3-(N-morpholino) propanesulfonic acid (MOPS) pH 7.0, 20 mM sodium acetate, 10 mM EDTA pH 8.0) under RNase-free conditions a final volume of 50 mL. CFPS samples were quenched by placing on ice and supplying with 1 µL Qiagen RNase Inhibitor (Qiagen, Valencia, Calif.) per 15-µL reaction. Samples ere immediately purified using Qiagen RNeasy MinElute Cleanup Kit (Qiagen). Total RNA was quantified using ThermoScientific NanoDrop 2000c (ThermoScientific, Waltham, Mass.). Twenty micrograms of total RNA, the bulk of which is ribosomal RNA, was mixed with 1× denaturing mix (1.3× loading buffer, 1.3× MOPS, 42% v/v deionized formamide, and 8.2% v/v formaldehyde) and adjusted to a final volume of 20 µL. Samples were heated to 70° C. for 10 min to denature any secondary structure, after which they were immediately placed on ice for 5 min. In addition, the denaturing gel was supplied with 100 V for 10 min before loading the RNA samples. After loading the RNA samples, the gel was supplied with 60 V for 2 h. The buffer was recirculated every 30 min. to prevent ion/pH gradients from forming. The gel was imaged with BioRad Gel Doe XR+ (BioRad, Hercules, Calif.) for GelRed staining.

Example 5 sfGFP Assay

The amount of active sfGFP produced was determined by adding 2 μL of CFPS sample to 100 μL of sfGFP assay buffer (100 mM HEPES-KOH pH 7.6, 14 mM magnesium acetate, 60 mM potassium acetate) in a black 96-well half-area plate. Samples were allowed to incubate in the assay buffer for 1 h before measuring total fluorescence to allow for complete protein folding during the time course assays. The total fluorescence was read using a BioTek Synergy 2 plate reader (Winooski, Vt.) with excitation/emission of 485/528 nm. Relative fluorescent units (RFUs) were recorded for each cell-free reaction. RFUs were compared to a linear standard curve made in house by expressing $^{14}$C-leucine labeled sfGFP in an *E. coli* PANOx CFPS reaction and relating trichloroacetic acid (TCA) precipitable soluble protein yield to RFUs (Jewett, M. C., Swartz, J. R., "Rapid expression and purification of 100 nmol quantities of active protein using cell-free protein synthesis," *Biotechnol. Prop.* 2004, 20:102-109).

Example 6

Creatine and Inorganic Phosphate Quantitative Assays

The quantitative analysis of creatine was performed using the EnzyChrom™ Creatine Assay Kit (BioAssay Systems, Hayward, Calif.). The quantitative analysis of inorganic phosphate was performed using the EnzChek® Phosphate Assay Kit (Life Technologies, Carlsbad, Calif.). For each kit, the CFPS samples were frozen on liquid nitrogen to quench the reaction and later thawed and assayed concurrently. To measure creatine concentration, samples were diluted 30-fold with water and compared to a linear creatine standard ranging from 0 to 1 mM. Absorbance was measured at 570 nm, following manufacturer's instructions with 100 μL reactions in a 96-well plate. To measure phosphate concentration, samples were diluted 500-fold with water and compared to a linear phosphate standard ranging from 0 to 150 μM Absorbance was read at 360 nm following the manufacturer's instructions. Nucleotide concentrations were determined by comparison to a standard calibration.

Example 7

Nucleotide and Amino Acid Concentration Quantitative HPLC Assay

HPLC analysis was used to measure nucleotide and amino acid concentrations. For both assays, 5% v/v TCA was added to the cell-free reaction mixture in a 1:1 volumetric ratio. Samples were centrifuged at 12,000×g for 15 min at 4° C. The supernatant was collected and samples were analyzed using an Agilent 1260 series HPLC system (Agilent, Santa Clara, Calif.).

For amino acid analysis, a ZORBAX Eclipse Plus column (4.6 mm×100 mm, 1.8 μm particle size; Agilent) was used with a Rapid Resolution HT derivitization method using o-phthalaldehyde (OPA) and fluorenyl ethyl chloroformate (FMOC). Separation was carried out at a flow rate of 1.0 mL min$^{-1}$ for 20 min. Mobile phase A contained 10 mM sodium borate, 10 mM sodium phosphate dibasic, and 5 mM sodium azide (pH 8.2 with HCl) and mobile phase B contained acetonitrile: ethanol:water in a 45:45:10 volumetric ratio. The buffer gradient for B was as follows: 0 min, 2%; 0.35 min, 2%; 16.4 min, 57%; 16.5 min, 100%; 17.7 min, 100%; 17.8 min, 2%; 20 min, end. Amino acids were detected at 262 and 338 nm. Amino acid concentrations were determined by comparison to a standard calibration.

For nucleotide analysis, a BioBasic AX column (4.6 mm×150 mm 5 μm particle size; Thermo Scientific, West Palm Beach, Fla.) was used for analysis. Separation was carried out at a flow rate of 0.75 mL min$^{-1}$. The method started with a mobile phase of 100% 5 mM Na$_2$HPO$_4$ (mobile phase A) and 0% 750 mM Na$_2$HPO$_4$ (mobile phase B), both adjusted to pH 3.2 with phosphoric acid. The buffer gradient for B was as follows: 0 min, 0%; 1.0 min, 40%; 40 min, 80%; 45 min, 100%; 47 min, 0%; 50 min, end. Nucleotides were detected at 254 nm.

INCORPORATION BY REFERENCE

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A method for calibrating a cell-free protein synthesis reaction for optimal activity, comprising:
   (a) providing a yeast cell extract competent for cell-free protein synthesis (CFPS);
   (b) performing a CFPS reaction with the extract;
   (c) measuring a first reaction end-point where in vitro protein synthesis plateaus;
   (d) measuring a second reaction end-point where Energy Charge of the extract declines to a level in a range from about 0.40 to about 0.80 of Energy Charge of a control extract, wherein the control extract is a separate extract not used in a CFPS reaction or the control extract is the extract provided for the CFPS reaction prior to performing the CFPS reaction;
   (e) after the Energy Charge of the extract provided for the CFPS reaction declines to a level in a range from about 0.40 to about 0.8 of the Energy Charge of the control extract, adjusting Energy Charge of the extract provided for the CFPS reaction to a level in a range from about 0.80 to about 1.0 of the control extract, wherein adjusting comprises adding to the extract a phosphate-containing energy source selected from ATP, creatine phosphate, and a combination thereof; and
   (f) removing a toxic metabolic byproduct from the CFPS reaction, wherein the toxic metabolic byproduct comprises inorganic phosphate.

2. The method of claim 1, wherein the extract competent for cell-free protein synthesis and the control extract comprise extracts derived from a common extract source.

3. The method of claim 1, wherein the yeast is Saccharomyces cerevisiae.

4. The method of claim 1, wherein adjusting the Energy Charge of the extract comprises adjusting the Energy Charge before a time selected from the first reaction end-point and second reaction end-point.

5. The method of claim 1, wherein adjusting the Energy Charge of the extract further comprises adding a phosphate-free energy source to the extract and the phosphate-free energy source is selected from the group consisting of glucose, starch and dextran.

6. The method of claim 1, wherein adjusting the Energy Charge of the extract further comprises adding cAMP to the extract.

7. The method of claim 1, wherein performing cell-free protein synthesis with the extract comprising performing a coupled transcription/translation reaction.

8. The method of claim 7, wherein the coupled transcription/translation reaction comprises an expression template comprising SEQ ID NO:6 and a polymerase comprising phage T7 DNA polymerase.

9. The method of claim 1, wherein the cell-free protein synthesis reaction is selected from a batch CFPS reaction or a semi-continuous CFPS reaction.

* * * * *